(12) United States Patent
Wang

(10) Patent No.: US 7,495,993 B2
(45) Date of Patent: Feb. 24, 2009

(54) ONBOARD DATA STORAGE AND METHOD

(75) Inventor: Kang-Huai Wang, Saratoga, CA (US)

(73) Assignee: Capso Vision, Inc., Saratoga, CA (US)

( * ) Notice: Subject to any disclaimer, the term of this patent is extended or adjusted under 35 U.S.C. 154(b) by 0 days.

(21) Appl. No.: 11/552,880

(22) Filed: Oct. 25, 2006

(65) Prior Publication Data

US 2007/0091713 A1 Apr. 26, 2007

Related U.S. Application Data

(60) Provisional application No. 60/760,794, filed on Jan. 19, 2006, provisional application No. 60/760,079, filed on Jan. 18, 2006, provisional application No. 60/739,162, filed on Nov. 23, 2005, provisional application No. 60/730,797, filed on Oct. 26, 2005.

(51) Int. Cl.
   *G11C 8/00* (2006.01)
(52) U.S. Cl. ............... 365/230.09; 365/233.1; 365/236; 365/239; 365/240
(58) Field of Classification Search ............ 365/230.09, 365/233.1, 236, 239, 240
   See application file for complete search history.

(56) References Cited

U.S. PATENT DOCUMENTS

| | | | |
|---|---|---|---|
| 3,387,286 A | 6/1968 | Dennard | |
| 3,404,376 A | 10/1968 | Brown | |
| 5,115,413 A * | 5/1992 | Sato et al. | 365/230.09 |
| 5,404,338 A | 4/1995 | Murai et al. | |
| 5,563,844 A * | 10/1996 | Takata et al. | 365/233.5 |
| 5,848,074 A | 12/1998 | Maeno | |
| 6,233,191 B1 | 5/2001 | Gould et al. | |
| 6,298,068 B1 | 10/2001 | Shyu | |
| 6,385,100 B2 * | 5/2002 | Noda et al. | 365/189.12 |
| 6,871,009 B1 | 3/2005 | Suzuki | |
| 2003/0085879 A1 | 5/2003 | Shi | |
| 2005/0124874 A1 | 6/2005 | Kawano et al. | |
| 2006/0250851 A1* | 11/2006 | Surico et al. | 365/185.19 |

* cited by examiner

*Primary Examiner*—Hoai V Ho
(74) *Attorney, Agent, or Firm*—Edward C. Kwok; MacPherson Kwok Chen & Heid LLP

(57) ABSTRACT

A semiconductor memory device and an associated method suitable for use in specific applications with predictable memory access pattern, such as in a capsule camera. The memory device takes advantage of the memory access pattern to simplify address processing circuit to realize savings in power and silicon area. Because random access to the semiconductor device is not required, the interface from external to the semiconductor device is also simplified by eliminating at least the address port that is used to specify the memory locations accessed. The method is applicable not only to non-volatile memory technologies (e.g., flash memory), it is also applicable to volatile memory technologies, such as transient charge storage-based memory circuits (e.g., DRAMs) and metastable states-based memory circuits (e.g., SRAMs).

38 Claims, 25 Drawing Sheets

| Value | Natural binary code | Grey code |
|---|---|---|
| 0 | 0000 | 0000 |
| 1 | 0001 | 0001 |
| 2 | 0010 | 0011 |
| 3 | 0011 | 0010 |
| 4 | 0100 | 0110 |
| 5 | 0101 | 0111 |
| 6 | 0110 | 0101 |
| 7 | 0111 | 0100 |
| 8 | 1000 | 1100 |
| 9 | 1001 | 1101 |
| 10 | 1010 | 1111 |
| 11 | 1011 | 1110 |
| 12 | 1100 | 1010 |
| 13 | 1101 | 1011 |
| 14 | 1110 | 1001 |
| 15 | 1111 | 1000 |

FIG. 7

| No. of YCK after reset | YR | Y0 | Y1 | | Y15 |
|---|---|---|---|---|---|
| 0 | 1 | 0 | 0 | | 0 |
| 1 | 0 | 1 | 0 | | 0 |
| 2 | 0 | 0 | 1 | | 0 |
| --- | --- | --- | --- | --- | --- |
| 16 | 0 | 0 | 0 | | 1 |

Fig. 10

ONBOARD DATA STORAGE AND METHOD

CROSS-REFERENCES TO RELATED APPLICATIONS

The present invention is related and claims priority to (1) U.S. Provisional Patent Application, entitled "In Vivo Autonomous Sensor with On-Board Data Storage," Ser. No. 60/730,797, filed on Oct. 26, 2005; (2) U.S. Provisional Patent Application, entitled "In Vivo Autonomous Sensor with On-Board Data Storage," Ser. No. 60/739,162, filed on Nov. 23, 2005; (3) U.S. Provisional Patent Application, entitled "In Vivo Autonomous Sensor with Panoramic Camera," Ser. No. 60/760,079, filed on Jan. 18, 2006; and (4) U.S. Provisional Patent Application, entitled "In Vivo Autonomous Sensor with On-Board Data Storage," Ser. No. 60/760,794, filed on Jan. 19, 2006. These U.S. Provisional Patent Applications (1)-(4) (collectively, the "Provisional Patent Applications") are hereby incorporated by reference in their entireties. The present application is also related to U.S. patent application (the "Copending Application"), entitled "In Vivo Autonomous Camera with On-Board Data Storage or Digital Wireless Transmission In Regulatory Approved Band," Ser. No. 11/533,304, and filed on Sep. 19, 2006. The Copending Application is hereby incorporated by reference in its entirety.

BACKGROUND OF THE INVENTION

1. Field of the Invention

The present invention relates to swallowable capsule cameras for imaging of the gastro-intestinal (GI) tract. In particular, the present invention relates to a memory system that is suitable for capsule camera applications.

2. Discussion of the Related Art

Devices for imaging body cavities or passages in vivo are known in the art and include endoscopes and autonomous encapsulated cameras. Endoscopes are flexible or rigid tubes that are passed into the body through an orifice or surgical opening, typically into the esophagus via the mouth or into the colon via the rectum. An image is taken at the distal end using a lens and transmitted to the proximal end, outside the body, either by a lens-relay system or by a coherent fiber-optic bundle. A conceptually similar instrument might record an image electronically at the distal end, for example using a CCD or CMOS array, and transfer the image data as an electrical signal to the proximal end through a cable. Endoscopes allow a physician control over the field of view and are well-accepted diagnostic tools. However, they have a number of limitations, present risks to the patient, are invasive and uncomfortable for the patient. The cost of these procedures restricts their application as routine health-screening tools.

Because of the difficulty traversing a convoluted passage, endoscopes cannot reach the majority of the small intestine and special techniques and precautions, that add cost, are required to reach the entirety of the colon. Endoscopic risks include the possible perforation of the bodily organs traversed and complications arising from anesthesia. Moreover, a trade-off must be made between patient pain during the procedure and the health risks and post-procedural down time associated with anesthesia. Endoscopies are necessarily inpatient services that involve a significant amount of time from clinicians and thus are costly.

An alternative in vivo image sensor that addresses many of these problems is capsule endoscopy. A camera is housed in a swallowable capsule, along with a radio transmitter for transmitting data, primarily comprising images recorded by the digital camera, to a base-station receiver or transceiver and data recorder outside the body. The capsule may also include a radio receiver for receiving instructions or other data from a base-station transmitter. Instead of radio-frequency transmission, lower-frequency electromagnetic signals may be used. Power may be supplied inductively from an external inductor to an internal inductor within the capsule or from a battery within the capsule.

An early example of a camera in a swallowable capsule is described in the U.S. Pat. No. 5,604,531, issued to the Ministry of Defense, State of Israel. A number of patents assigned to Given Imaging describe more details of such a system, using a transmitter to send the camera images to an external receiver. Examples are U.S. Pat. Nos. 6,709,387 and 6,428,469. There are also a number of patents to the Olympus Corporation describing a similar technology. For example, U.S. Pat. No. 4,278,077 shows a capsule with a camera for the stomach, which includes film in the camera. U.S. Pat. No. 6,939,292 shows a capsule with a memory and a transmitter.

An advantage of an autonomous encapsulated camera with an internal battery is that the measurements may be made with the patient ambulatory, out of the hospital, and with only moderate restrictions of activity. The base station includes an antenna array surrounding the bodily region of interest and this array can be temporarily affixed to the skin or incorporated into a wearable vest. A data recorder is attached to a belt and includes a battery power supply and a data storage medium for saving recorded images and other data for subsequent uploading onto a diagnostic computer system.

A typical procedure consists of an in-patient visit in the morning during which clinicians attach the base station apparatus to the patient and the patient swallows the capsule. The system records images beginning just prior to swallowing and records images of the GI tract until its battery completely discharges. Peristalsis propels the capsule through the GI tract. The rate of passage depends on the degree of motility. Usually, the small intestine is traversed in 4 to 8 hours. After a prescribed period, the patient returns the data recorder to the clinician who then uploads the data onto a computer for subsequent viewing and analysis. The capsule is passed in time through the rectum and need not be retrieved.

The capsule camera allows the GI tract from the esophagus down to the end of the small intestine to be imaged in its entirety, although it is not optimized to detect anomalies in the stomach. Color photographic images are captured so that anomalies need only have small visually recognizable characteristics, not topography, to be detected. The procedure is pain-free and requires no anesthesia. Risks associated with the capsule passing through the body are minimal—certainly the risk of perforation is much reduced relative to traditional endoscopy. The cost of the procedure is less than for traditional endoscopy due to the decreased use of clinician time and clinic facilities and the absence of anesthesia.

As the capsule camera becomes a viable technology for inspecting gastrointestinal tract, various methods for storing the image data have emerged. For example, U.S. Pat. No. 4,278,077 discloses a capsule camera that stores image data in chemical films. U.S. Pat. No. 5,604,531 discloses a capsule camera that transmits image data by wireless to an antenna array attached to the body or provided in the inside a vest worn by a patient. U.S. Pat. No. 6,800,060 discloses a capsule camera that stores image data in an expensive atomic resolution storage (ARS) device. The stored image data could then be downloaded to a workstation, which is normally a personal computer for analysis and processing. The results may then be reviewed by a physician using a friendly user interface. However, these methods all require a physical media conversion during the data transfer process. For example, image data on chemical film are required to be converted to a physical digital medium readable by the personal computer. The wireless transmission by electromagnetic signals requires extensive processing by an antenna and radio frequency electronic circuits to produce an image that can be stored on a computer. Further, both the read and write operations in an ARS device rely on charged particle beams.

A capsule camera using a semiconductor memory device, whether volatile or nonvolatile, has the advantage of being capable of a direct interface with both a CMOS or CCD image sensor, where the image is captured, and a personal computer, where the image may be analyzed. The high density and low manufacturing cost achieved in recent years made semiconductor memory the most promising technology for image storage in a capsule camera. According to Moore's law, which is still believed valid, density of integrated circuits double every 24 months. Even though CMOS or CCD sensor resolution doubles every few years, the data density that can be achieved in a semiconductor memory device at least keeps pace with the increase in sensor resolution. Alternatively, if the same resolution is kept, a larger memory allows more images to be stored and therefore can accommodate a higher frame rate.

In a high density memory cell array (e.g., a 1-T DRAM[1] or a nonvolatile memory cell), necessary peripheral circuits that are used for addressing the memory cells typically occupy a significant area of the integrated circuit die ("chip"). In a semiconductor memory circuit, addressing signals propagate over metal wires ("buses") over substantially the entire chip area to connect the large number of decoding circuits required for a large memory array. The addressing signals dissipate an amount of power that may be estimated by the expression $P=\frac{1}{2} CV^2$, where V is the supply voltage, and C is the capacitance loading of the signal wires. The capacitance loading has two components: wire capacitance and circuit loading capacitance (e.g., gate capacitance and junction capacitance). As a result, address decoding on a semiconductor memory device is a power-consuming operation. Furthermore, the parallel address lines and the decoding circuits they connect all occupy valuable semiconductor area.

[1] The data storage portion of an 1-T DRAM cell consists of a single MOS transistor configured as a capacitor.

FIGS. 5A and 5B illustrate an exemplary decoding scheme used in a conventional semiconductor device. For the purpose of illustration only, FIGS. 5A and 5B show 10-bit addresses including a 6-bit row address $A_{12} \ldots A_7$ and a 4-bit column address $A_3 \ldots A_0$. Even then, the row and column addresses are carried by 20 address lines (i.e., each address bit requires a signal line for itself and its complement), coupled to a large number of decoder logic gates that drive the word lines (FIG. 5A) and the bit lines (FIG. 5B). The memory device shown in FIGS. 5A and 5B is organized as a "×8" device (i.e., each address selects an 8-bit byte). "×1" and "×16" are examples of other popular configurations. In the current generation of semiconductor devices, such as a gigabit device, the complexity is significantly higher. As the requirement for additional address lines and decoding circuits, the required die area and capacitance increase correspondingly. Significant power is therefore dissipated by decoding circuits and conductive paths in a semiconductor device.

SUMMARY OF THE INVENTION

One embodiment of the present invention provides a semiconductor memory device and an associated method suitable for use in specific applications with predictable memory access pattern, such as in a capsule camera. The memory device takes advantage of the memory access pattern to simplify address processing circuit to realize savings in power and silicon area. Because random access to the semiconductor device is not required, the interface from external to the semiconductor device is also simplified by eliminating at least the address port that is used to specify the memory locations accessed. The present invention is applicable not only to non-volatile memory technologies (e.g., flash memory), it is also applicable to volatile memory technologies, such as transient charge storage-based memory circuits (e.g., DRAMs) and metastable states-based memory circuits (e.g., SRAMs).

In one embodiment, the semiconductor device includes a memory array with memory cells that are addressed by selectively activating word lines and bit lines. The memory array is addressed according to a predetermined address sequence, rather than randomly. The address sequence is generated by a counter in response to a clock signal from a pulse generator. The address sequence may be the same for both reading and writing.

According to one embodiment the column addresses are activated in sequence by shifting a set bit through a shift register in response to the clock signal, after a suitable delay to allow the memory array to be set up for reading or writing.

According to one embodiment of the present invention, the semiconductor memory device may be divided into blocks and within each block, into sections. The driver circuits for activating word line within a block are typically separate from driver circuits for word lines in another block. The bit lines of the blocks may be activating in sequence by shifting a set bit through a shift register. In one access sequence, the sections may be accessed section by section, moving from one section to a next section after all memory cells corresponding to only a single word of the one section is accessed. Alternatively, the memory device may be accessed block by block, moving from one block to a next block after all memory cells in the one block is accessed.

As mentioned above, the semiconductor memory device may be suitable for use in a capsule camera application. According to one embodiment of the present invention, the capsule camera may include a housing adapted to be swallowed, a light source within the housing, and a camera within the housing for capturing digital images of a scene illuminated by the light source. To maximize effectiveness of the space available in the semiconductor device, the capsule camera may further include a motion detector that detects a motion based on a difference between the digital images, and a motion evaluator that determines whether or not the storing later digital images is necessary. The predetermined memory access pattern eliminates a need for an address port that allows an external access device to specify memory locations. The interface to the semiconductor device is thereby greatly simplified, and facilitates an efficient design for accessing the semiconductor device to upload its contents.

The present invention is better understood upon consideration of the detailed description below in conjunction with the accompanying drawings.

BRIEF DESCRIPTION OF THE DRAWINGS

FIG. 7 shows table 700, which illustrates the bit patterns of a 4-bit Gray counter.

FIG. 10 shows successive bit patterns on output terminals $Y_{15}Y_{14} \ldots Y_0$ of shift register 901 of FIG. 9.

To facilitate cross-referencing among the figures, like elements in the figures are provided like reference numerals.

DETAILED DESCRIPTION OF THE INVENTION

The Copending Patent Application discloses a capsule camera that overcomes many deficiencies of the prior art. Today, semiconductor memories are low-cost, low-power, easily available from multiple sources, and compatible with application specific integrated circuit (ASIC), sensor electronics (i.e., the data sources), and personal computers (i.e., the data destination) without format conversion devices. One embodiment of the present invention allows images to be stored in an "on-board storage" using semiconductor memories which may be manufactured using industry standard memory processes, or readily available memory processes. To optimize the use of the semiconductor memory device for diagnostic image storage, a method of the present invention may detect camera motion to control the number of images stored in the semiconductor memory device.

According to one embodiment of the present invention, a specialized frame buffer is provided. As a 640×480 resolution VGA-type image has 300,000 pixels, and if each such pixel is represented equally by one byte of data (e.g., 8 bits), the image requires a 2.4 M-bit frame buffer ("regular frame buffer"). Because of its physical and power constraints, in practice, a capsule camera can provide only a fraction of the regular frame buffer. A highly efficiency image compression[2] algorithm to reduce the storage requirement may be provided, taking into consideration the limited processing power and limited memory size available in the capsule. As discussed in the Copending Patent Application, "partial frame buffers" may be provided, with each partial frame buffer being significantly smaller than a regular frame buffer. As the per-bit size in memory circuits continues to decrease, a method of the present invention may use the larger memory size made possible to achieve greater sensor resolution.

[2] The digital image may be compressed using a suitable lossy compression technique.

Figure 1:
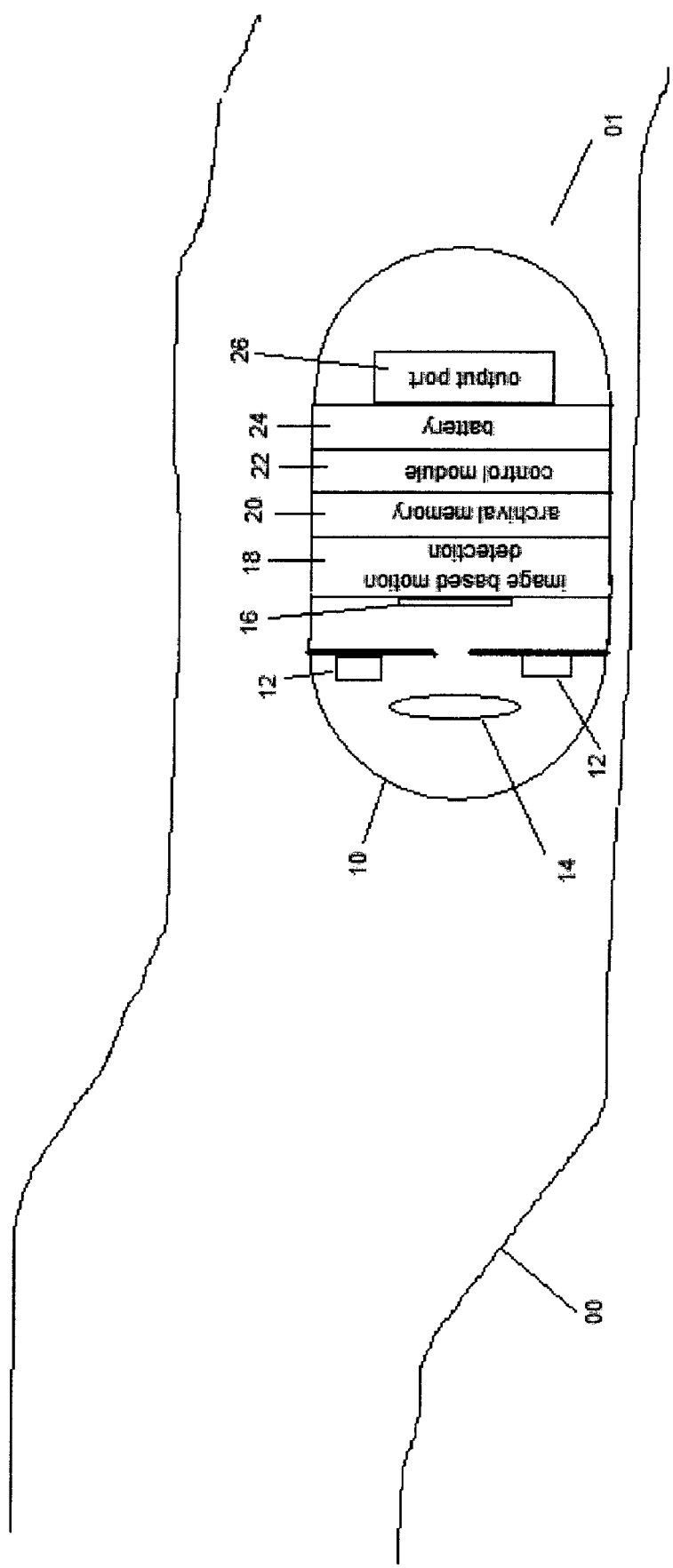
FIG. 1 shows schematically capsule system 01 in the GI tract, according to one embodiment of the present invention, showing the capsule in a body cavity.

FIG. 1 shows a swallowable capsule system 01 inside body lumen 00, in accordance with one embodiment of the present invention. Lumen 00 may be, for example, the colon, small intestines, the esophagus, or the stomach. Capsule system 01 is entirely autonomous while inside the body, with all of its elements encapsulated in a capsule housing 10 that provides a moisture barrier, protecting the internal components from bodily fluids. Capsule housing 10 is transparent, so as to allow light from the light-emitting diodes (LEDs) of illuminating system 12 to pass through the wall of capsule housing 10 to the lumen 00 walls, and to allow the scattered light from the lumen 00 walls to be collected and imaged within the capsule. Capsule housing 10 also protects lumen 00 from direct contact with the foreign material inside capsule housing 10. Capsule housing 10 is provided a shape that enables it to be swallowed easily and later to pass through the GI tract. Generally, capsule housing 10 is sterile, made of non-toxic material, and is sufficiently smooth to minimize the chance of lodging within the lumen.

As shown in FIG. 1, capsule system 01 includes illuminating system 12 and a camera that includes optical system 14 and image sensor 16. An image captured by image sensor 16 may be processed by image-based motion detector 18, which determines whether the capsule is moving relative to the portion of the GI tract within the optical view of the camera. Image-based motion detector 18 may be implemented in software that runs on a digital signal processor (DSP) or a central processing unit (CPU), in hardware, or a combination of both software and hardware. Image-based motion detector 18 may have one or more partial frame buffers, a semiconductor non-volatile archival memory 20 may be provided to allow the images to be retrieved at a docking station outside the body, after the capsule is recovered. System 01 includes battery power supply 24 and an output port 28. Capsule system 01 may be propelled through the GI tract by peristalsis.

Illuminating system 12 may be implemented by LEDs. In FIG. 1, the LEDs are located adjacent the camera's aperture, although other configurations are possible. The light source may also be provided, for example, behind the aperture. Other light sources, such as laser diodes, may also be used. Alternatively, white light sources or a combination of two or more narrow-wavelength-band sources may also be used. White LEDs are available that may include a blue LED or a violet LED, along with phosphorescent materials that are excited by the LED light to emit light at longer wavelengths. The portion of capsule housing 10 that allows light to pass through may be made from bio-compatible glass or polymer.

Optical system 14, which may include multiple refractive, diffractive, or reflective lens elements, provides an image of the lumen walls on image sensor 16. Image sensor 16 may be provided by charged-coupled devices (CCD) or complementary metal-oxide-semiconductor (CMOS) type devices that convert the received light intensities into corresponding electrical signals. Image sensor 16 may have a monochromatic response or include a color filter array such that a color image may be captured (e.g. using the RGB or CYM representations). The analog signals from image sensor 16 are preferably converted into digital form to allow processing in digital form. Such conversion may be accomplished using an analog-to-digital (A/D) converter, which may be provided inside the sensor (as in the current case), or in another portion inside capsule housing 10. The A/D unit may be provided between image sensor 16 and the rest of the system. LEDs in illuminating system 12 are synchronized with the operations of image sensor 16. One function of control module 22 is to control the LEDs during image capture operation.

Motion detection module 18 selects an image to retain when the image shows enough motion relative to the previous image in order to save the limited storage space available. The images are stored in an on-board archival memory system 20. The output port 26 shown in FIG. 1 is not operational in vivo but uploads data to a work station after the capsule is recovered, having passed from the body. Motion detection can also be used to regulate the image capture rate (i.e., the frequency at which the camera captures an image). It is desirable to increase the capture rate when the capsule is in motion. If capsule remains at the same place, it may be desirable to capture an image less frequently to save battery power.

Figure 2:
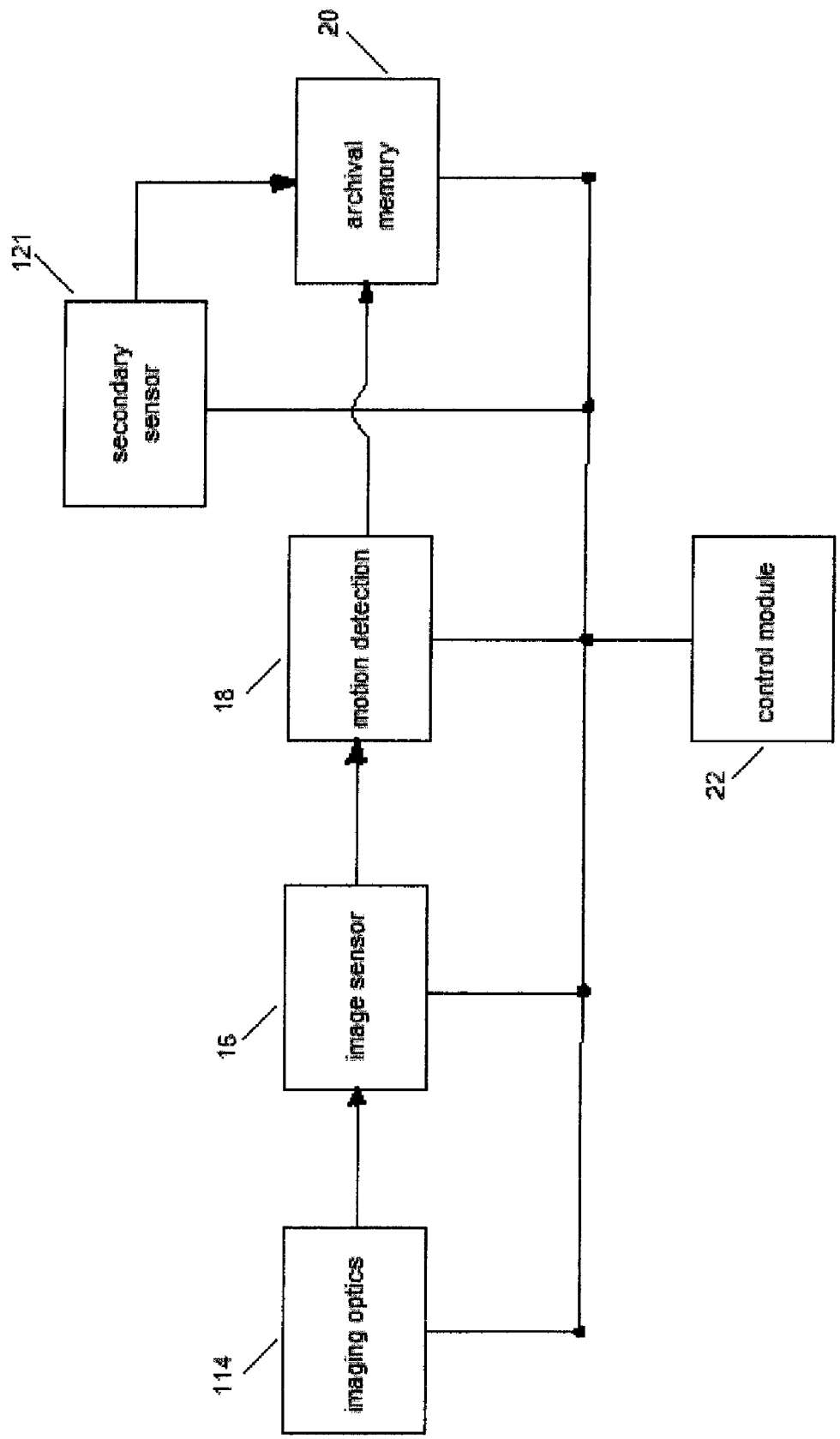
FIG. 2 is a functional block diagram of information flow during capsule camera operation in capsule system 01.

FIG. 2 is a functional block diagram of information flow during capsule camera operation. Except for optical system 114, all of these functions may be implemented on a single integrated circuit. As shown in FIG. 2, optical system 114, which represents both illumination system 12 and optical system 14, provides an image of the lumen wall on image sensor 16. Some images will be captured but not stored in the archival memory 20, based on the motion detection circuit 18, which decides whether or not the current image is sufficiently different from the previous image. An image may be discarded if the image is deemed not sufficiently different from a previous image. Secondary sensors (e.g., pH, thermal, or pressure sensors) may be provided. The data from the secondary sensors are processed by the secondary sensor circuit 121 and provided to archival memory system 20. Measurements made may be provided time stamps. Control module 22, which may consist of a microprocessor, a state machine or random logic circuits, or any combination of these circuits, controls the operations of the modules. For example, control module 22 may use data from image sensor 16 or motion detection circuit 18 to adjust the exposure of image sensor 16.

Archival memory system 20 can be implemented by one or more non-volatile semiconductor memory devices. Archival memory system 20 may be implemented as an integrated circuit separate from the integrated circuit on which control module 22 resides Since the image data are digitized for digital image processing techniques, such as motion detection, memory technologies that are compatible with digital data are selected. Of course, semiconductor memories that are mass-produced using planar technology (which represents virtually all integrated circuits today) are the most convenient. Semiconductor memories are most compatible because they share common power supply with the sensors and other circuits in capsule system 01, and require little or no data conversion when interfaced with an upload device at output port 26. Archival memory system 20 preserves the data collected during the operation, after the operation while the capsule is in the body, and after the capsule has left the body, up to the time the data is uploaded. This period of time is generally less than a few days. A non-volatile memory is preferred because data may be held without power consumption, even after the capsule's battery power has been exhausted. Suitable non-volatile memory includes flash memories, write-once memories, or program-once-read-once memories. Alternatively, archival memory system 20 may be volatile and static (e.g., a static random access memory (SRAM) or its variants, such as VSRAM, PSRAM). Alternately, the memory could be a dynamic random access memory (DRAM).

Archival memory 20 may be used to hold any initialization information (e.g., boot-up code and initial register values) to begin the operations of capsule system 01. The cost of a second non-volatile or flash memory may therefore be saved. That portion of the non-volatile memory can also be written over during operation to store the selected captured images.

Figure 3:
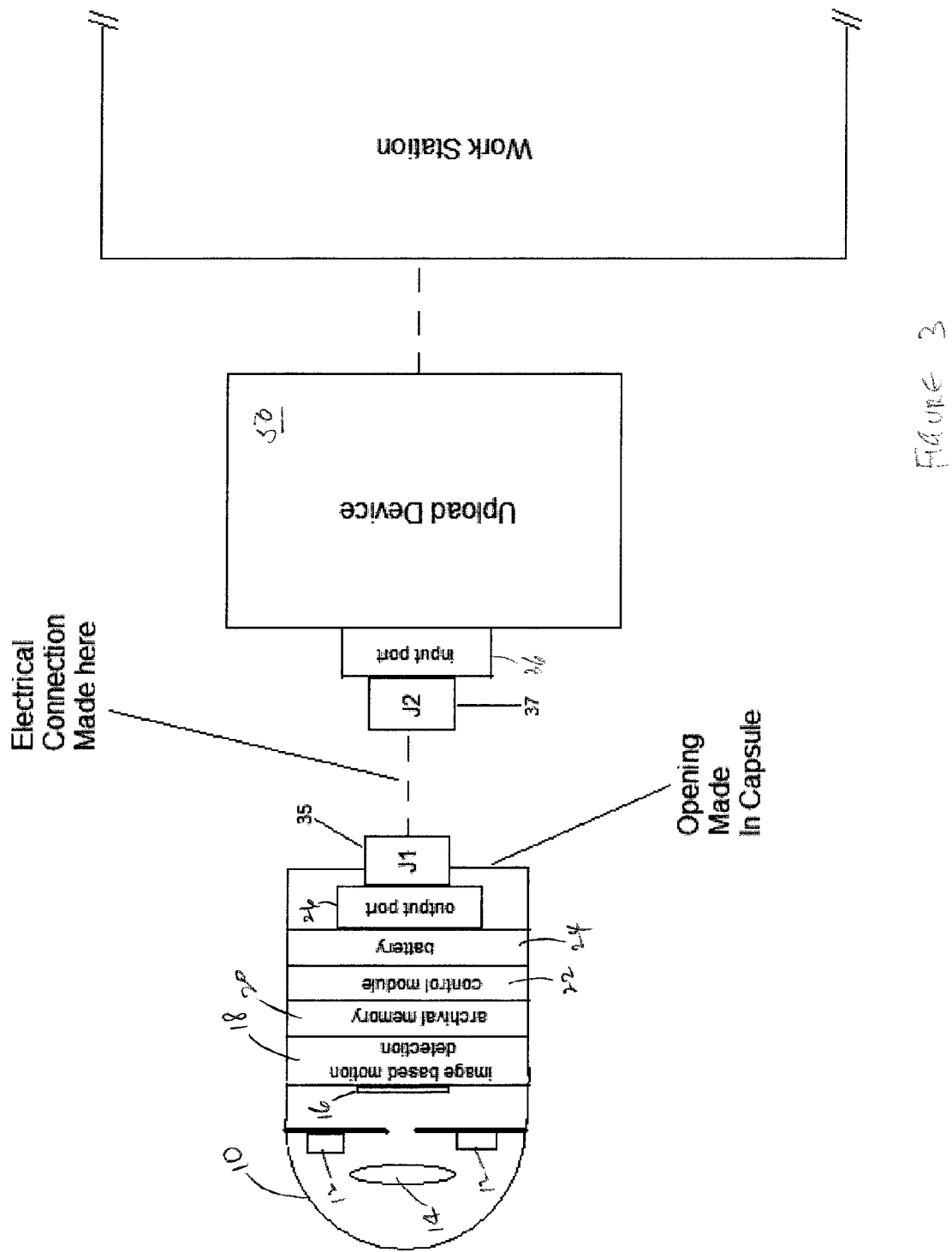
FIG. 3 is a functional block diagram illustrating the data transferring process from capsule system 01 to a workstation.

After the capsule passes from the body, it is retrieved. Capsule housing 10 is opened and input port 16 is connected to an upload device for transferring data to a computer workstation for storage and analysis. The data transferring process is illustrated in the functional block diagram of FIG. 3. As shown in FIG. 3, output port 26 of capsule system 01 includes an electrical connector 35 that mates with connector 37 at an input port of an upload device. Although shown in FIG. 3 to be a single connector, these connectors may be implemented as several conductors to allow data to be transferred serially or over a parallel bus, and so that power may be transferred from the upload device to the capsule, thereby obviating the need for the capsule battery to provide power for data uploading.

To make the electrical connection to output port 26, capsule housing 10 may be breached by breaking, cutting, melting, or another technique. Capsule housing 10 may include two or more parts that are pressure-fitted together, possibly with a gasket, to form a seal, but that can be separated to expose connector 35. The mechanical coupling of the connectors may follow the capsule opening process or may be part of the same process. These processes may be achieved manually, with or without custom tooling, or may be performed by a machine automatically or semi-automatically.

Figure 4:
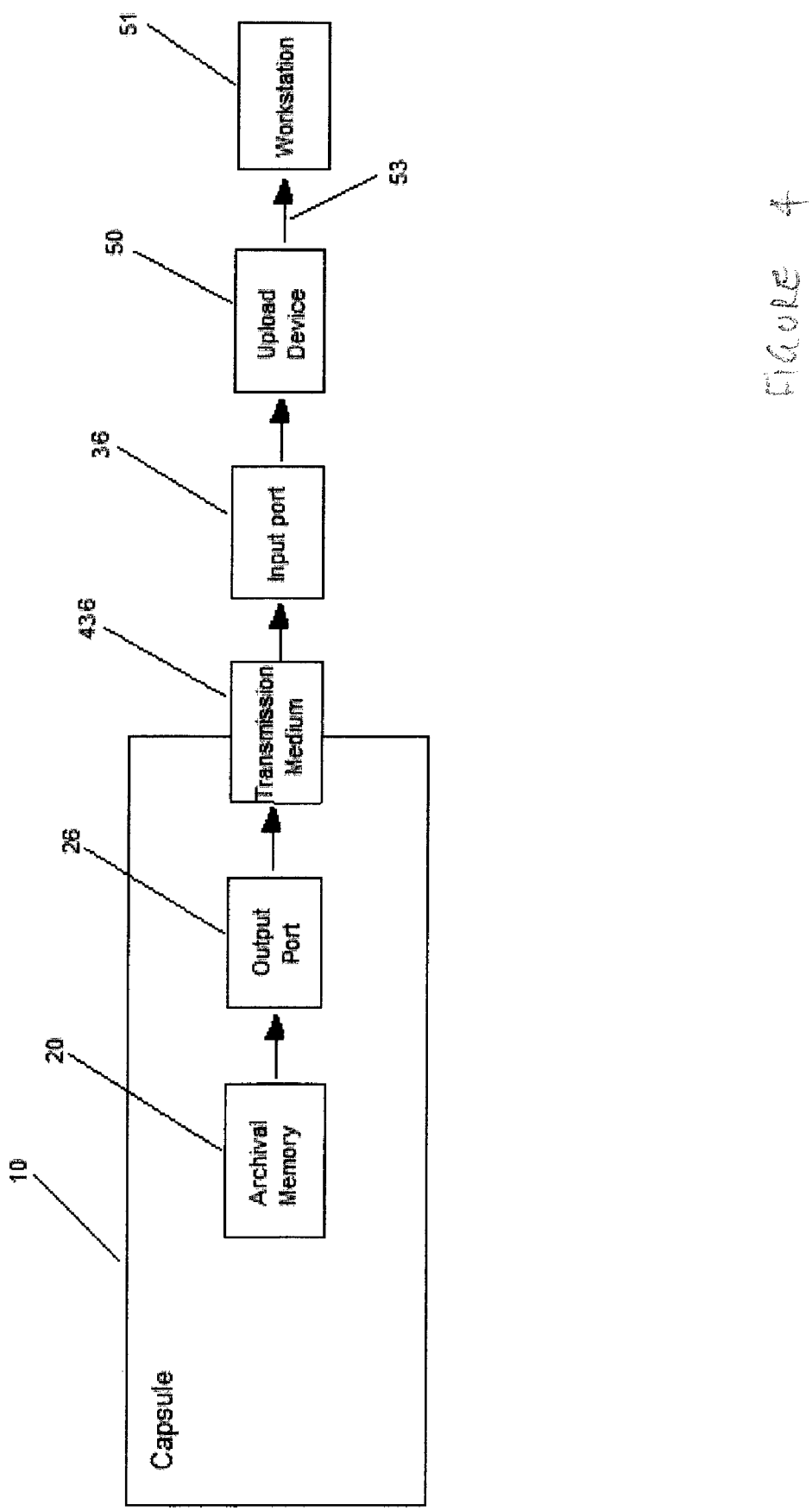
FIG. 4 is a functional block diagram illustrating the data upload process from a capsule, showing information flow from capsule system 01 to workstation 51.

FIG. 4 illustrates the data transfer process, showing information flow from capsule system 01 to workstation 51, where it is written into a storage medium such as a computer hard drive. As shown in FIG. 4, data is retrieved from archival memory 20 over transmission medium 43 between output port 26 of capsule system 01 and input port 36 of upload device 50. The transmission link may use established or custom communication protocols. The transmission medium may include the connectors 35 and 37 shown in FIG. 3 and may also include cabling not shown in FIG. 3. Upload device 50 transfers the data to a computer workstation 51 through interface 53, which may be implemented by a standard interface, such as a USB interface. The transfer may also occur over a local-area network or a wide-area network. Upload device 50 may have memory to buffer the data.

The present invention provides a semiconductor memory that is especially suitable for a capsule camera application. The semiconductor memory of the present invention may be implemented in any available semiconductor memory technology, such as DRAMs, SRAMs or electrically programmable non-volatile memory (e.g., flash memory).

In a capsule camera application, the memory device is either written (e.g., when the captured images are being recorded) or read (i.e., when the recorded images are uploaded). The present invention recognizes that, for such an application, it is sufficient that the memory cells in the memory device are accessed in a predictable sequence for read or write accesses—i.e., random access is not normally required. Taking advantage of this access characteristic, a semiconductor memory of the present invention includes a new address circuit with an associated addressing scheme that is both low-power and efficient in silicon area. The address circuit has a simple construction that obviates an address port, when accessed from outside the memory device, and avoids the large number of address lines and decoding circuits of the prior art. As battery life is a critical and precious resource in a capsule camera, a low-power address circuit for the on-board memory serves extends battery life. An address circuit that is efficient in silicon area allows a larger more silicon real estate for the memory array, resulting in greater image capacity, a smaller form factor, or both. A smaller form factor facilitates a smaller capsule design that is more comfortable for the patient.

Figure 5A:
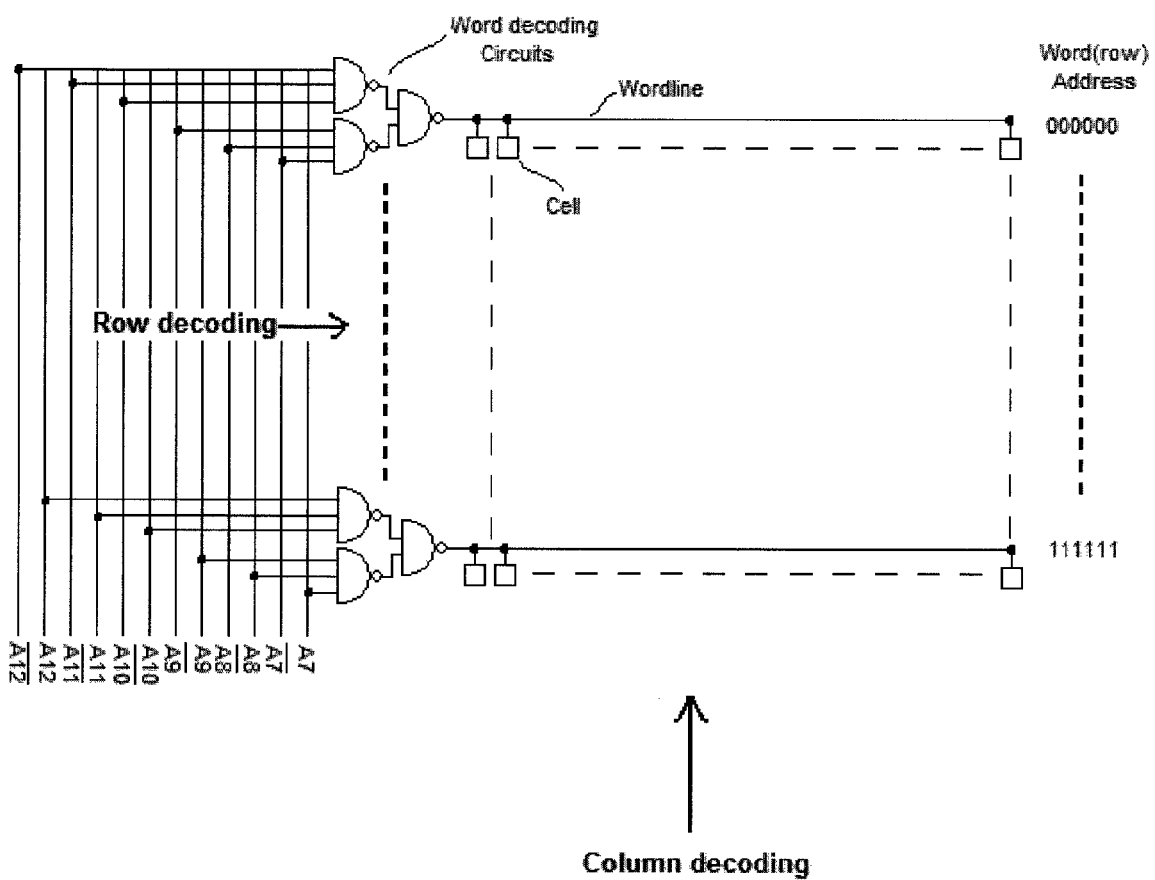
FIGS. 5A and 5B illustrate an exemplary decoding scheme used in a conventional semiconductor device.
Figure 5B:
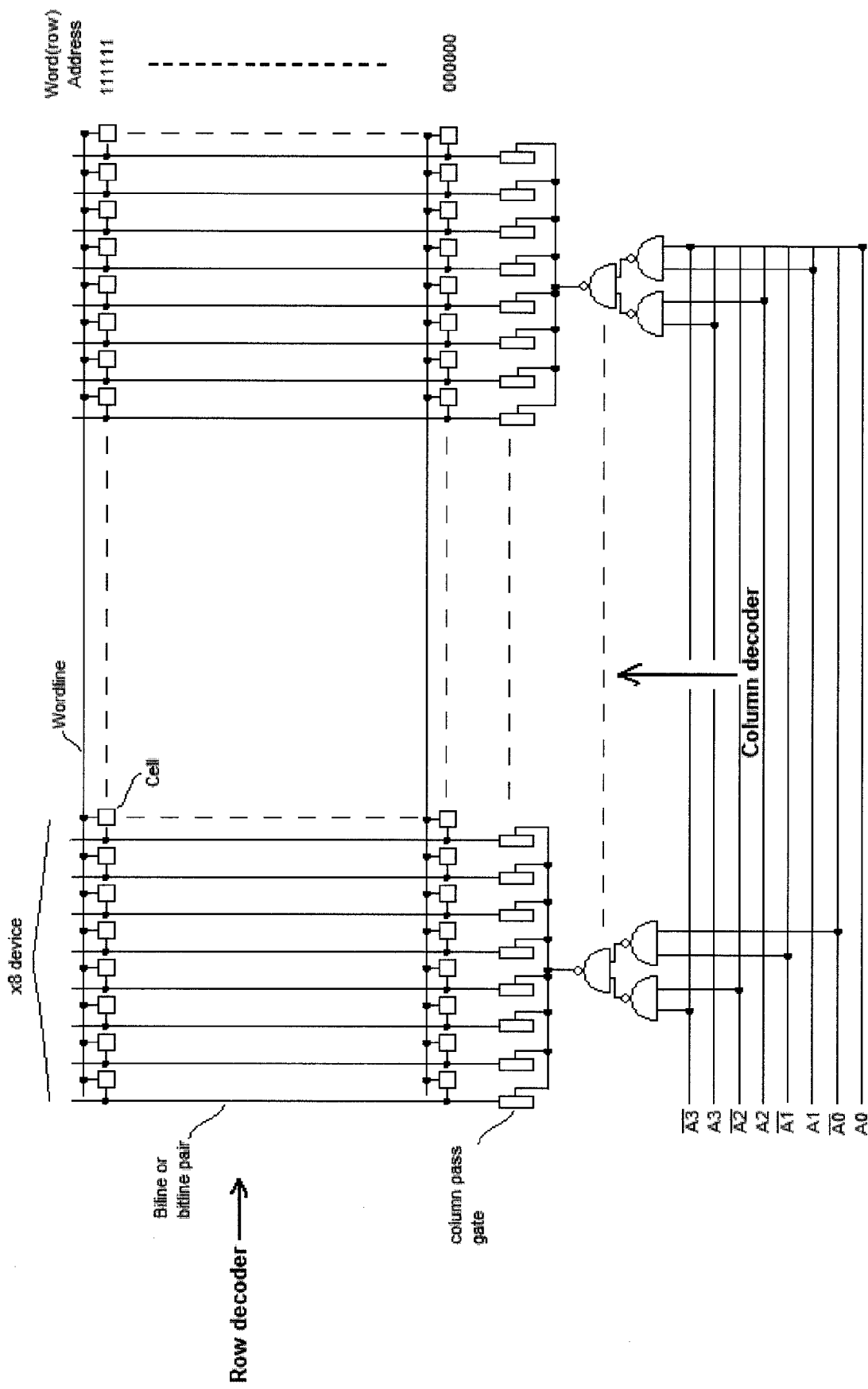
Figure 6A:
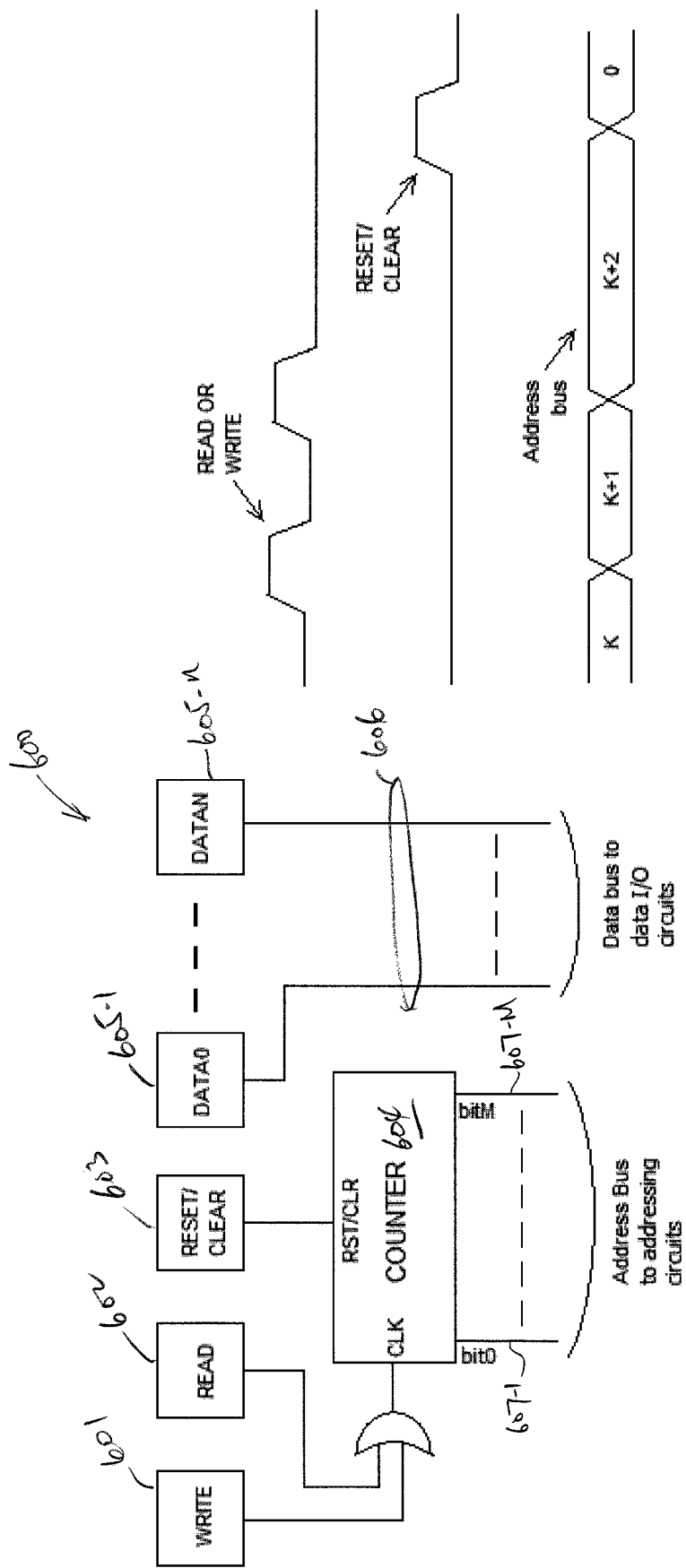
FIG. 6A shows address circuit 600, in accordance with one embodiment of the present invention.

FIG. 6A shows address circuit 600, in accordance with one embodiment of the present invention. Address circuit 600 may be used to generate addresses for conventional address decoders of a conventional memory device, such as the memory device of FIGS. 5A and 5B. As shown in FIG. 6A, address circuit 600 includes counter 604, write terminal 601 for receiving a pulse indicating a "write" operation for the memory device, read terminal 602 for receiving a pulse indicating a "read" operation for the memory device, and clear or reset terminal 603 for receiving a pulse indicating a "reset" or "clear" operation. The pulses for write terminal 601, read terminal 602 and clear or reset terminal 603 are generated elsewhere, such as from a write pulse generator, a read pulse generator, and a reset or clear pulse generator on a separate integrated circuit. The read/write data are provided on data bus 606, which are coupled to data input/output (I/O) circuits through I/O terminals 605-1 to 605-n.

As shown in FIG. 6A, counter 604 receives an input clock signal which is a sequence of pulses generated on either write terminal 601 or read terminal 602. With each pulse, counter 604 generates a new bit pattern at its output lines 607-0 to 607-M. Address circuit 600 thus generates $2^{M+1}$ addresses. Counter 604 may be a conventional binary counter. Alternatively, counter 604 may a Gray counter, which generates addresses differing only one in a single bit position between successive counts. As compared to a binary counter, a Gray counter saves power because only one of its output lines is driven to change state in each clock period. To illustrate, table 700 of FIG. 7 shows the bit patterns of a 4-bit Gray counter. Bit patterns of Gray counters of greater output lengths are known to those skilled in the art. A pulse at the clear or reset terminal 603 initializes counter 604 to an initial bit pattern (e.g., all zeroes). The timing diagram in FIG. 6A shows two read or write pulses generated by either write pulse generator 601 or read pulse generator 602 provide two successive addresses K+1 and K+2 at the output terminals of counter 604, and a reset pulse from reset or clear circuit 603 resets output terminals to all zeroes.

Figure 6B:
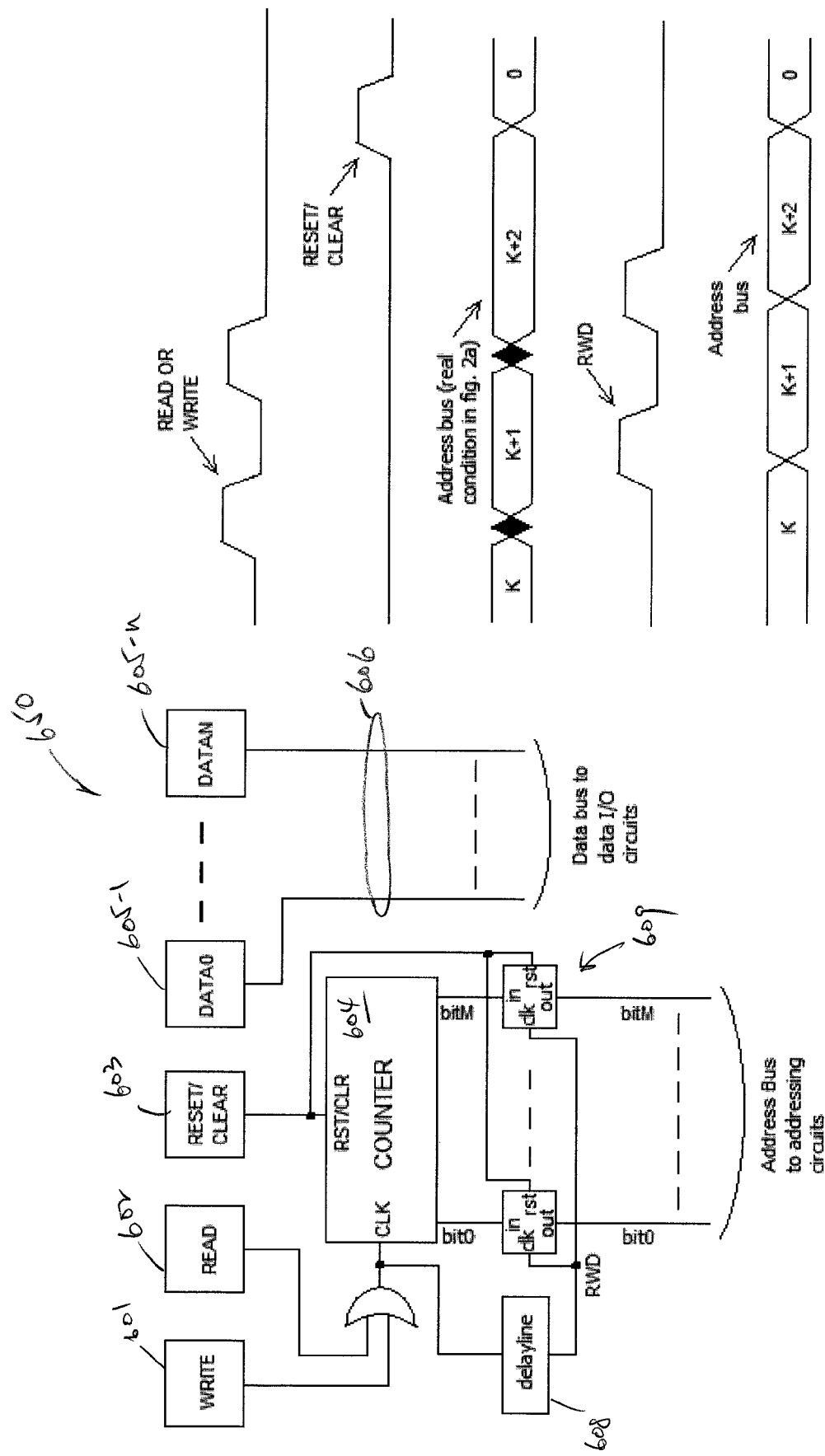
FIG. 6B shows address circuit 650, providing an output register to counter 604 of address circuit 600.

FIG. 6B shows address circuit 650 in which register 609—which may be implemented by a set of flip-flops connected in parallel—latches the output signals of counter 604 after a predetermined delay of the clock signal from write terminal 601 or read terminal 602. Address circuit 650 has an advantage over address circuit 600 because the output signals of counter 604 typically require some time after receiving the clock signal to settle ("clock to output delay"). During this time, without register 609, the output signals of address counter 604 may cause numerous signal glitches, which may result in transient states being propagated over the long address buses through the large decoding circuits, thereby dissipating power unnecessarily. Techniques such as pulsed word line or bit line may alleviate the problem. These techniques, however, do not alleviate the large capacitive loads on the address signals. In address circuit 650, the predetermined delay of delay element 608 is designed to be greater than the clock to output delay of counter 604, thereby preventing the output signals of counter 604 from propagating to the rest of the semiconductor memory device until after the address signals from counter 604 settle.

Figure 6C:
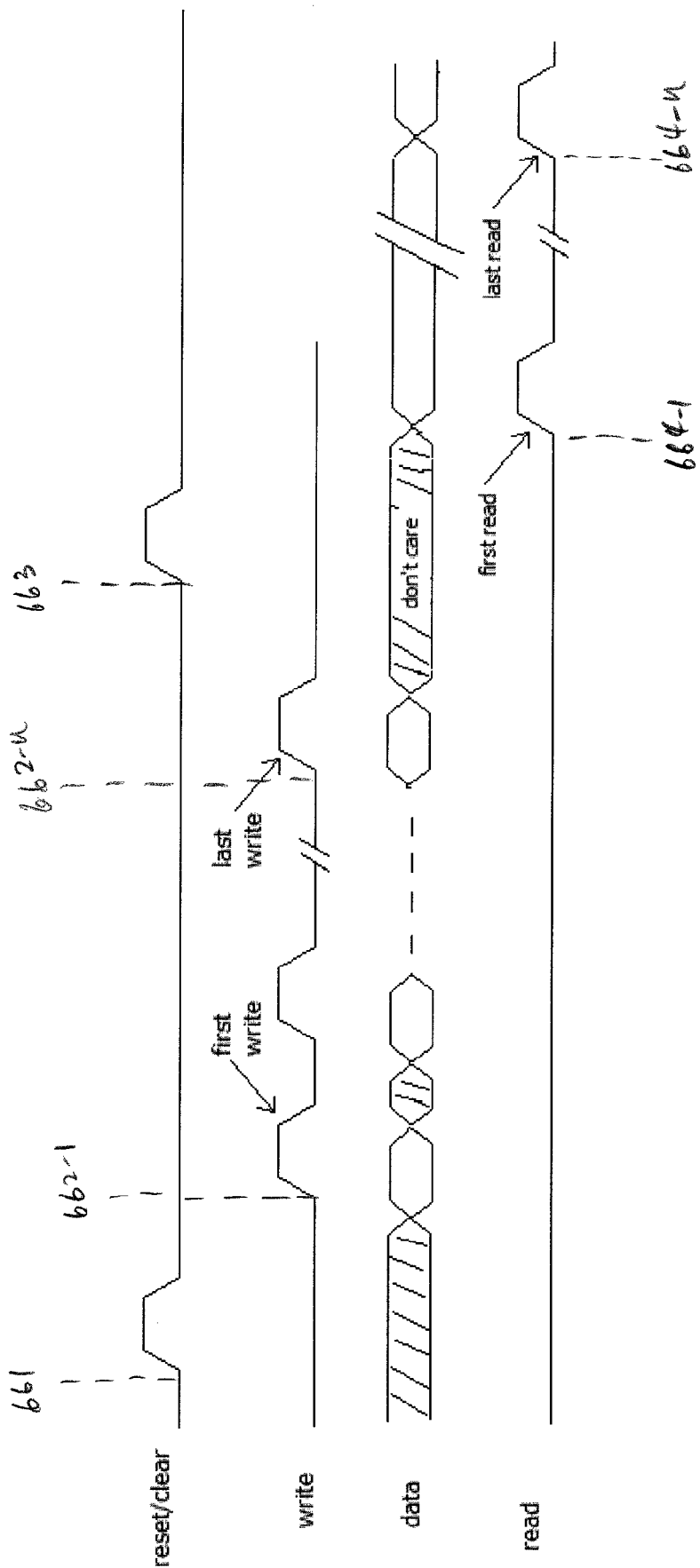
FIG. 6C shows one example of using address circuit 600, in accordance with one embodiment of the present invention.

FIG. 6C shows one example of using address circuit 600, in accordance with one embodiment of the present invention. Initially, at time 661, at some time after the capsule is swallowed, a reset or clear signal initializes the generated address at counter 604 to the first location of the semiconductor memory device. As the capsule travels through the GI tract, images are captured, placed onto data bus 606, and written into the semiconductor memory device according to write pulses 662-1 to 662-n on write terminal 601. During this time, the semiconductor memory device is not read. After the capsule is recovered, the image data are uploaded, as discussed above. Prior to reading the semiconductor memory device, a reset or clear signal is applied at time 663 to initializes the generated address at counter 604 to the first memory location of the semiconductor memory device. During the upload process, at times 664-1 to 664-n, the memory device is read according to read pulses on read terminal 602, but not written. The semiconductor memory device drives the content at each memory location on to data bus 606. Because the semiconductor memory device is not randomly accessed, the sequence in which data is received or provided is known, and thus an address port is not necessary to access the memory device. For example, control module 22 of FIG. 2 need not provide an address to the memory device. Consequently, the number of wiring connections between the memory device and the application specific integrated circuit (ASIC), on which control module 22 may be provided is much reduced. The assembly of the capsule camera is thus made easier, and the power that is required to drive addressing signals between integrated circuits is saved. This power saving can be significant, as the capacitance of connections between integrated circuits is typically much greater than connections within an integrated circuit. Moreover, the voltages at the terminals between integrated circuits (e.g., 3.3-5.0 volts) are typically much higher than the voltages within an integrated circuit (e.g., 1.3-3.3 volts). Thus, the power dissipation according to $P=\frac{1}{2}CV^2$ is also avoided.

Address circuit 600 is advantageous even when compared to a system in which the wire connections between the integrated circuits are shared between data and address under a multiplexing scheme, as such a multiplexing scheme require additional logic and timing circuits to implement the multiplexing. Moreover, under a multiplexing scheme, power is expended in data I/O circuits for driving both address and data between the integrated circuits. Under the addressing scheme of address circuit 600, only data is required to be driven between the integrated circuits.

Figure 8:
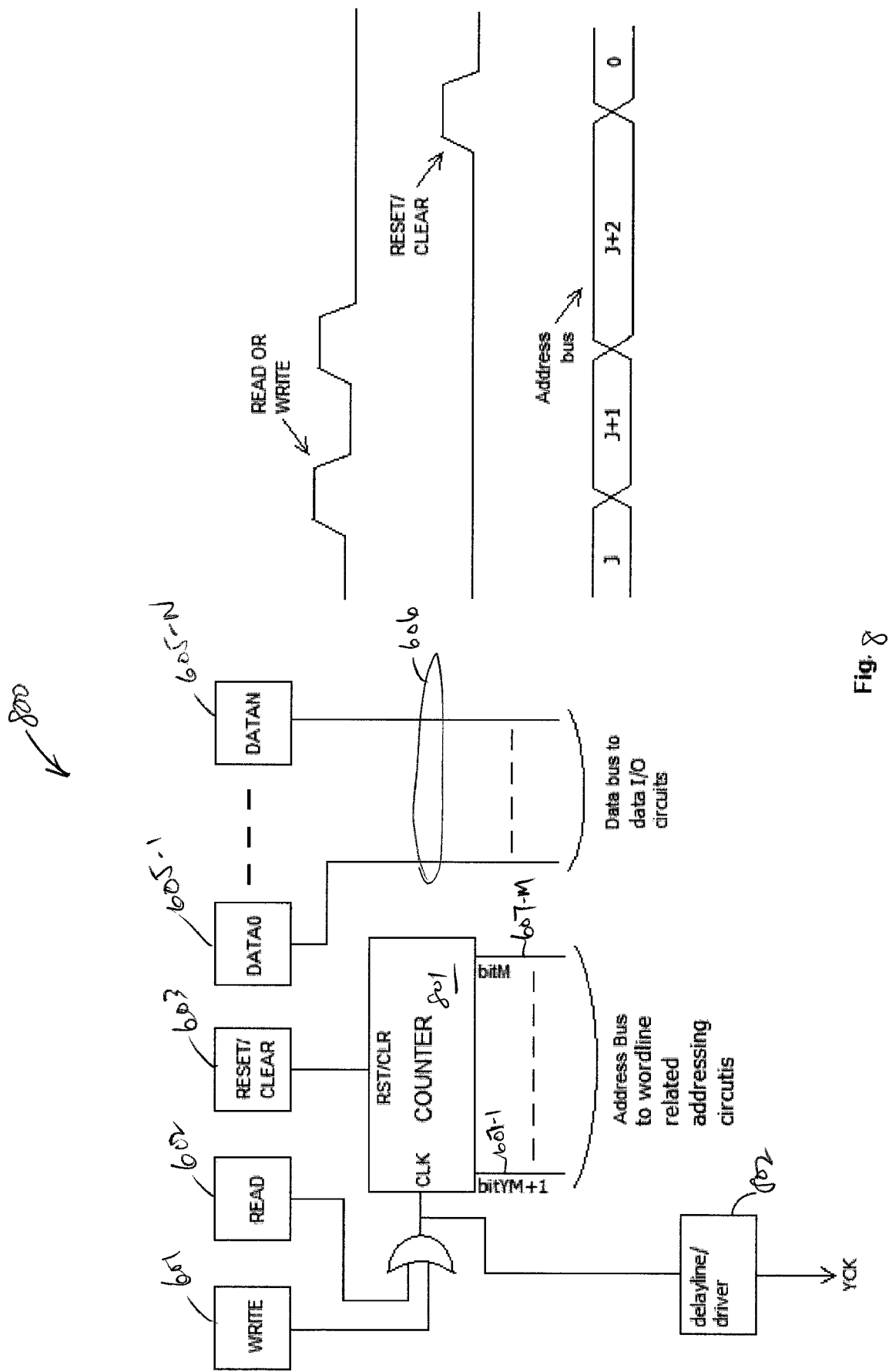
FIG. 8 shows address circuit 700, in accordance with a second embodiment of the present invention.

FIG. 8 shows address circuit 800, in accordance with another embodiment of the present invention. Address circuit 800 is substantially similar to address circuit 600, except that, unlike counter 604 of address circuit 600 of FIG. 6, counter 801 provides only the row addresses to drive the word lines of a memory array. The read or write pulses from write pulse generator 601 or read pulse generator 602 are each delayed by delay element 802 to generate a clock signal for a shift register, such as shift register 901 of FIG. 9.

Figure 9:
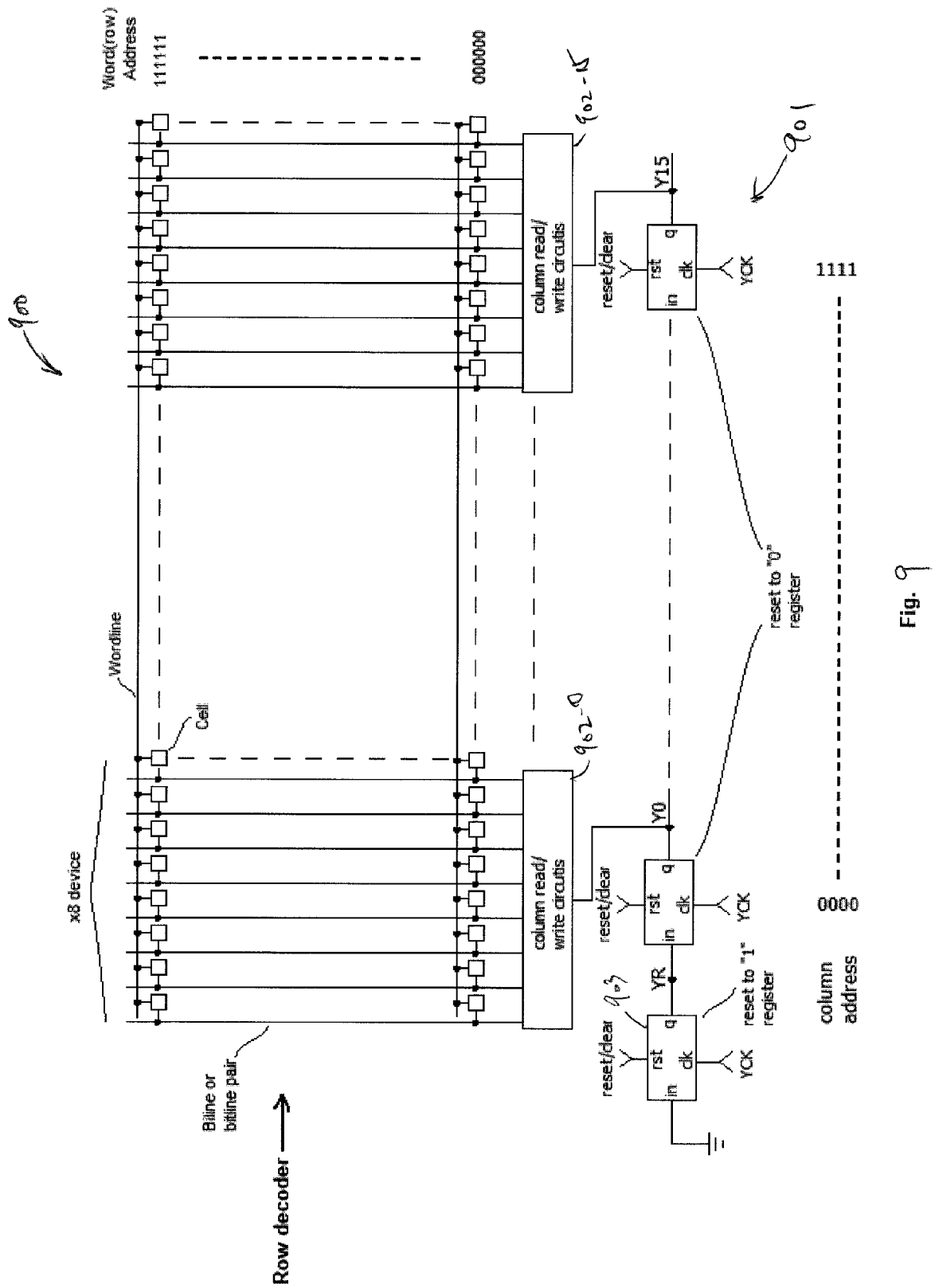
FIG. 9 shows memory array 900, in accordance with one embodiment of the present invention.

FIG. 9 shows memory array 900, in accordance with one embodiment of the present invention. As shown in FIG. 9, rather than a conventional decoder circuit to decode a column address to drive bit lines of memory array 900, the decoded signals for the bit lines are provided by shift register 901. As shown in FIG. 9, shift register 901 can be provided by serially connected flip-flops. The output bit pattern $Y_{15}Y_{14} \ldots Y_0$ for shift register 901 consists of all '0s' except for a single bit position, where it is set, so as to activate read/write circuits 902-0 to 902-15. The set bit can be provided by a reset or clear signal to register element 903 from reset or clear terminal 603. For illustrative purpose only, shift register 901 provides an output bit pattern of 16 bits. Each of read/write circuits 902-0 to 902-15 activates a single bit or a group of bits, depending on the organization of memory array 900 (e.g., ×1, ×8 or ×16). For illustrative purpose only, memory array 900 is shown to have a ×8 organization. Delay element 802 provides a suitable amount of delay after activation for the word line to provide "self-timing." Self-timing is a known technique practiced in memory design to allow time for various memory array activities, such as bit-line "pre-charge."

Shift register 901 replaces the large number of column address lines and decoder circuits of the prior art. As a result, savings in both power and silicon area are achieved, as large capacitance in addresses buses running over large distances and decoding circuits are avoided.

Figure 11:
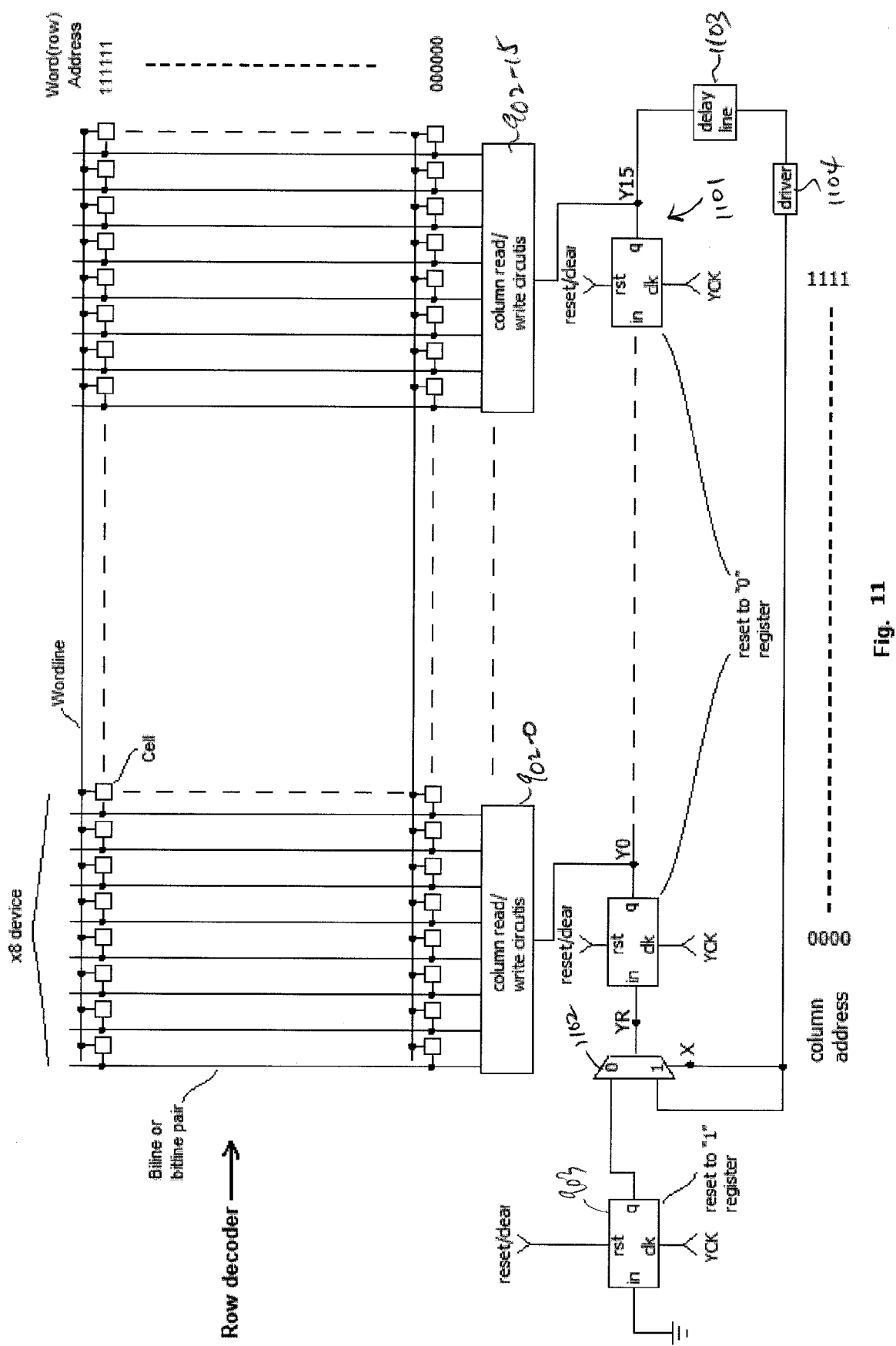
FIG. 11 shows alternative shift register 1101, which may be provided in place of shift register 901 of FIG. 9 for continuous access over multiple word lines.

At the start of operation and every 16 cycles, a reset circuit (not shown) resets shift register 901 to an initial state in which input node YR (to the flip-flop that provides bit $Y_0$) is set to '1', while the output bits of shift register 901 are set to '0'. With each read or write pulse, the '1' bit is shifted successive to the right (i.e., from bit $Y_0$ towards bit $Y_{15}$) to activate one of read/write circuits 902-0 to 902-15, such as shown in FIG. 10. FIG. 11 shows alternative shift register 1101, which may be provided in place of shift register 901 of FIG. 9. As shown in FIG. 11, the output bit $Y_{15}$ is circulated back to the input of the register element for bit $Y_0$ through multiplexer 1102. Output bit $Y_{15}$ (driven by driver 1104 to node X) delayed by delay element 1103 to meet the hold time requirement of the register element that provides bit $Y_0$, selects every 16 cycles the '1' bit back to input node YR of the register element that provides bit $Y_0$. Shift register 1101 need not be provided a reset circuit separate from reset or clear circuit 603, as required in address circuit 900.

Figure 12:
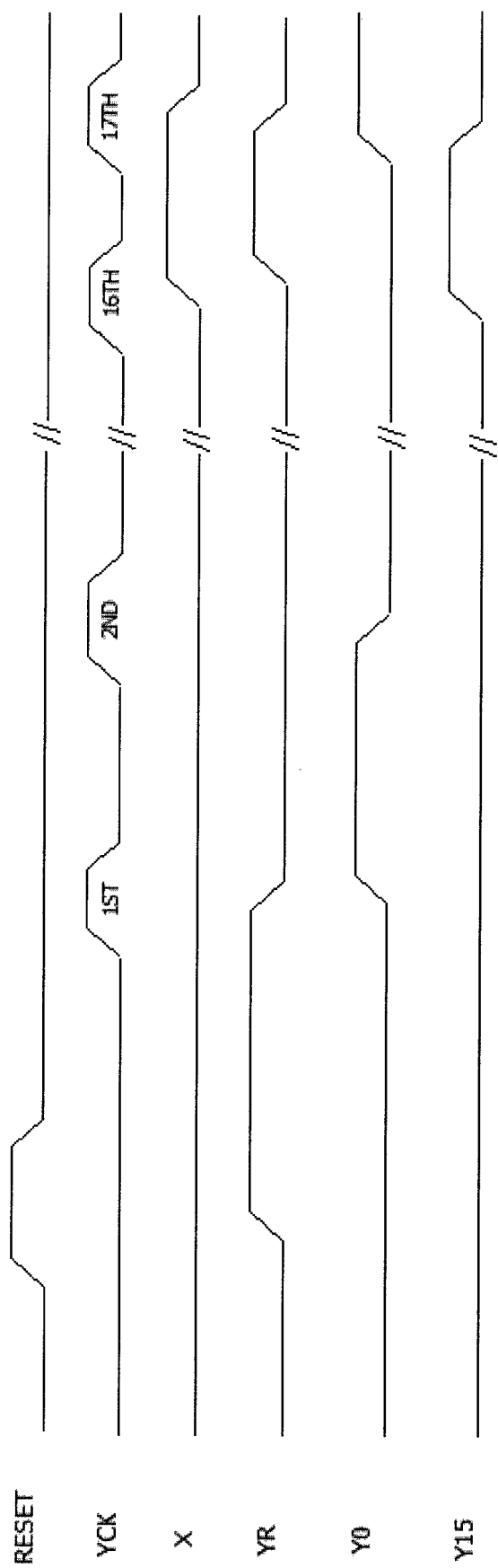
FIG. 12 shows the waveforms for the reset signal, the shift clock YCK to shift register 1101, select signal of multiplexer 1102 at node X, input node YR of the flip-flop that provides bit $Y_0$, and output bit $Y_{15}$.

FIG. 12 shows the waveforms for the reset signal, the shift clock YCK to shift register 1101, select signal of multiplexer 1102 at node X, input node YR of the register element that provides bit $Y_0$, and output bit $Y_{15}$. As shown in FIG. 12, after reset, node YR is set to logic '1'. A write or read pulse provided as clock YCK latches the '1' bit into shift register 1101 at output bit $Y_0$, while the '0' bit at node X (output bit $Y_{15}$) resets the logic value at node YR. Successive pulses on YCK shifts the '1' bit through shift register 1101. After the $16^{th}$ write or read pulse, the logic value at YR becomes '1' again.

Figure 13A:
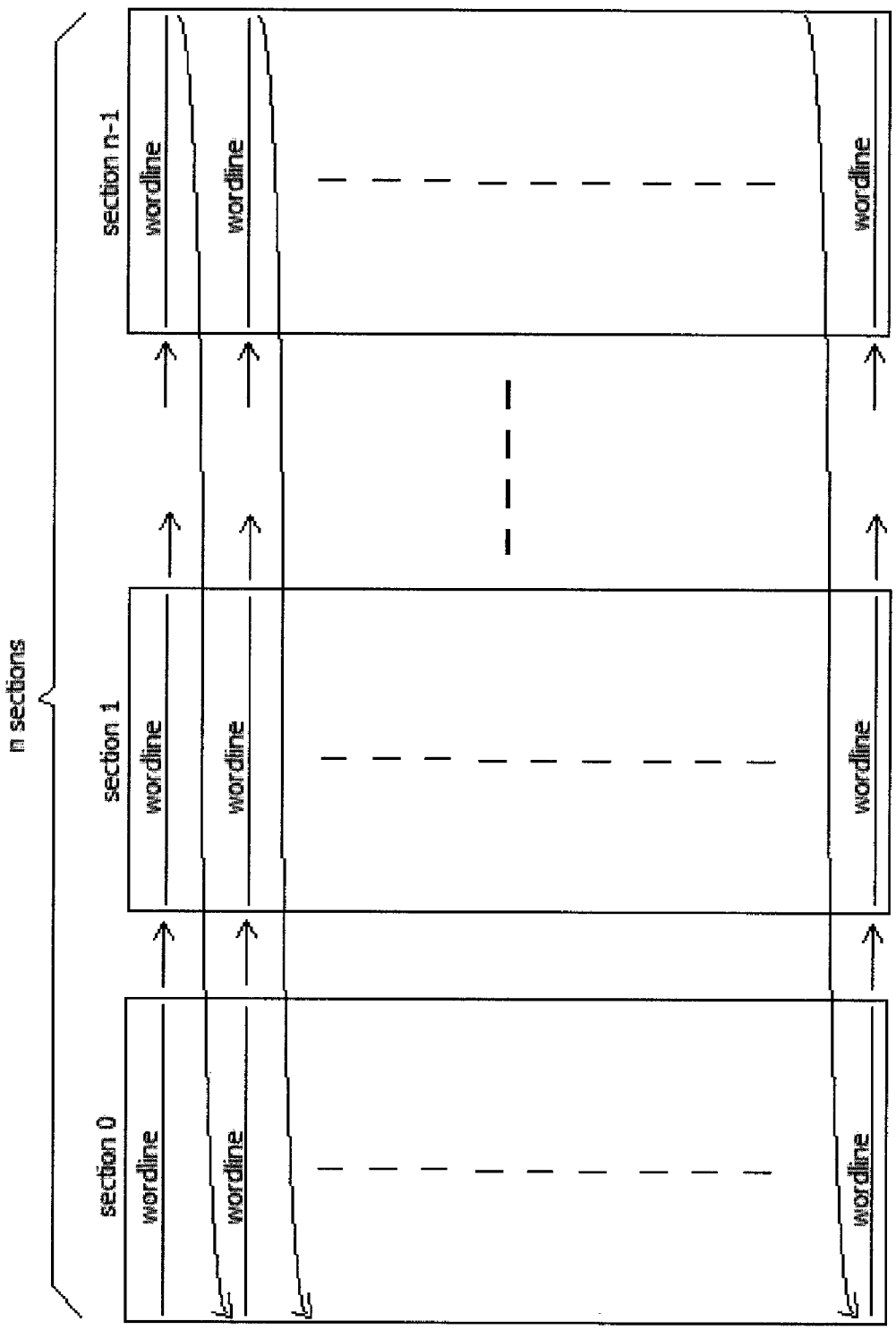
FIG. 13A shows an addressing sequence for block 1300 of a memory device, which is organized into n sections, in accordance with one embodiment of the present invention; the addressing sequence of FIG. 13A activates one word line in each section before accessing the next section.

A memory device is often divided in blocks and, within a block, may be divided into sections. Each section within a block may provide a memory array of the type shown, for example, in FIG. 9. FIG. 13A shows an organization of block 1300 of a memory device, including n sections, in accordance with one embodiment of the present invention. FIG. 13A also shows an addressing sequence in which the sections are activated in succession along corresponding word lines, moving to the next sections after cycling through the column addresses in the current section once. For each section, the row address—corresponding to a new set of corresponding word lines—changes when the section is activated.

Such an addressing scheme may be supported by providing, in each section of block 1300, a shift register structure similar to shift register structure 1101 of FIG. 11, with some modifications. In section 0 of block 1300, the input terminal to the register element providing output bit $Y_0$ receives an input value selected by multiplexer 1102 between the output value of reset register 903 (which resets to value '1'), or the output value $Y_{15}$ circulated back from section (n−1) of block 1300. At block (n−1) of block 1300, the output bit $Y_{15}$ is delayed by delay element 1103 and driven by driver 1104 back to the data and select input terminals of multiplexer 1102 of section 0. Except for section (n−1), each section provides its output bit $Y_{15}$ to the input terminal of the register element for bit $Y_0$ in the next section. For example, bit $Y_{15}$ of section 0 is provided to the input terminal of the register element for bit $Y_0$ for section 1.

Figure 13B:
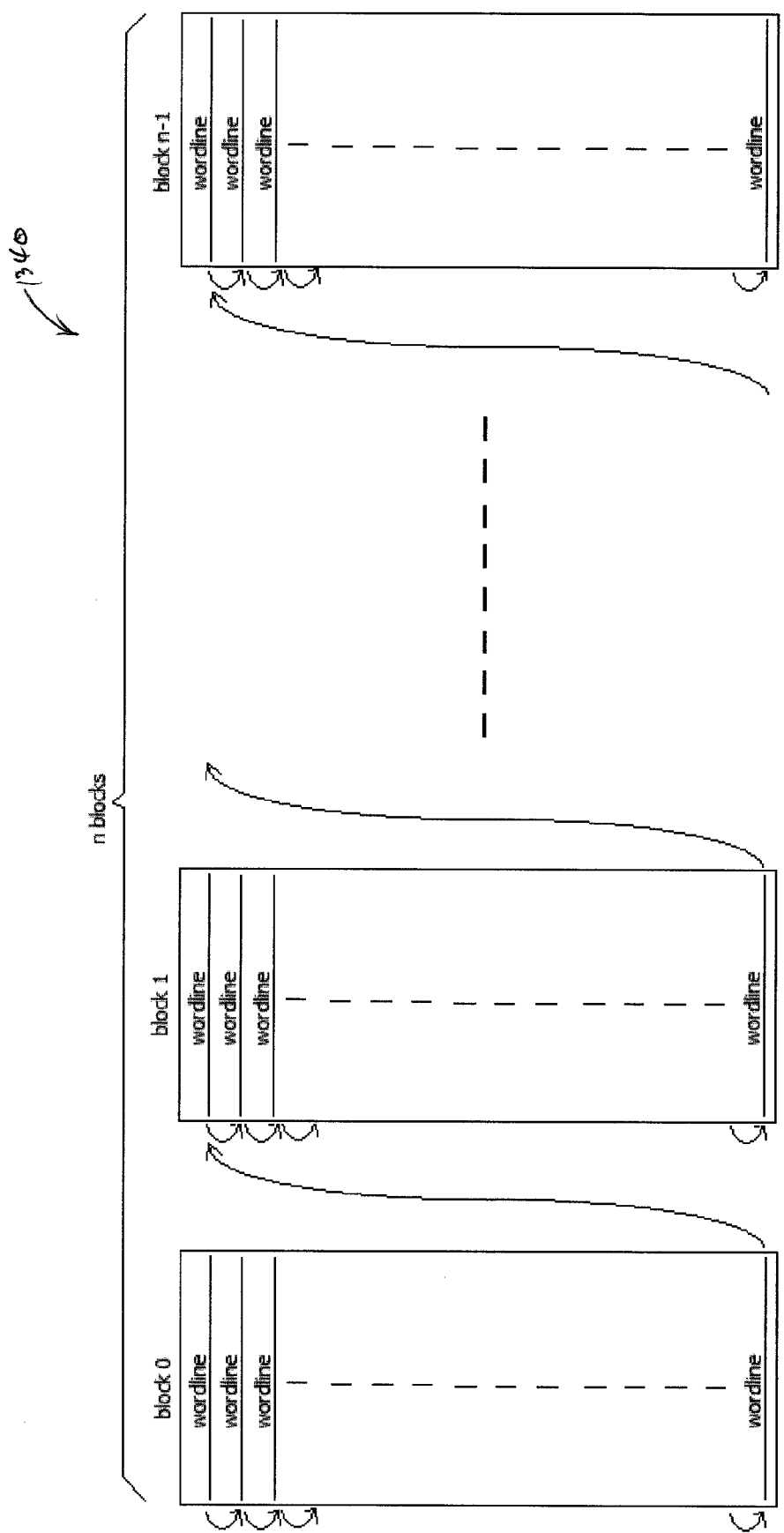
FIG. 13B shows an addressing sequence for memory device 1340; the addressing sequence of FIG. 13B accesses every memory cell in each block before accessing the next block.
Figure 13E:
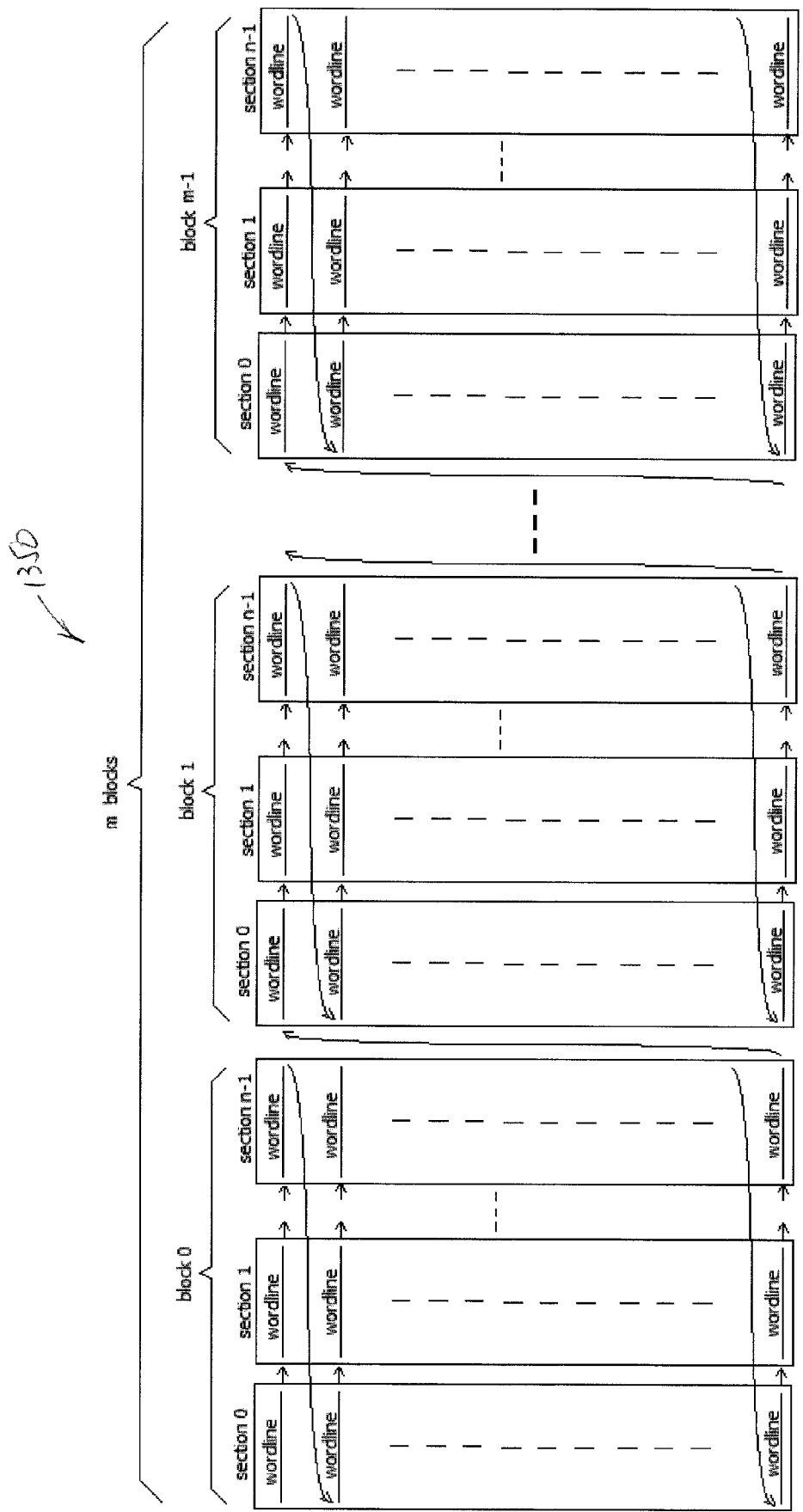
FIG. 13C shows an addressing sequence for memory device 1350, which is more complex than the addressing sequence shown in FIGS. 13A and 13B.
Figure 14A:
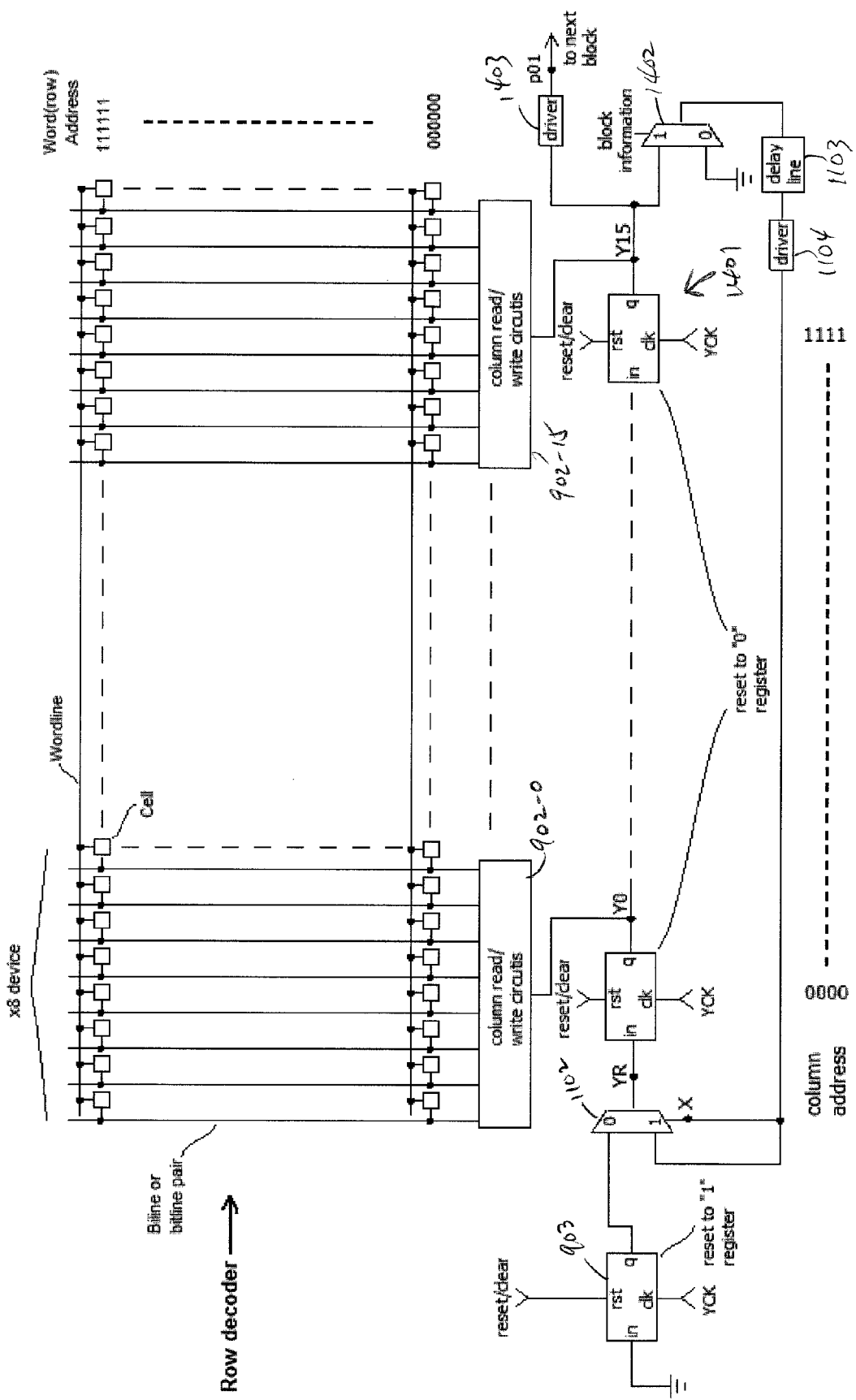
FIGS. 14A and 14B show, respectively, shift register structures for use in the first section of a memory block and in any of the subsequent sections, for supporting the address sequences of FIG. 13A.
Figure 14B:
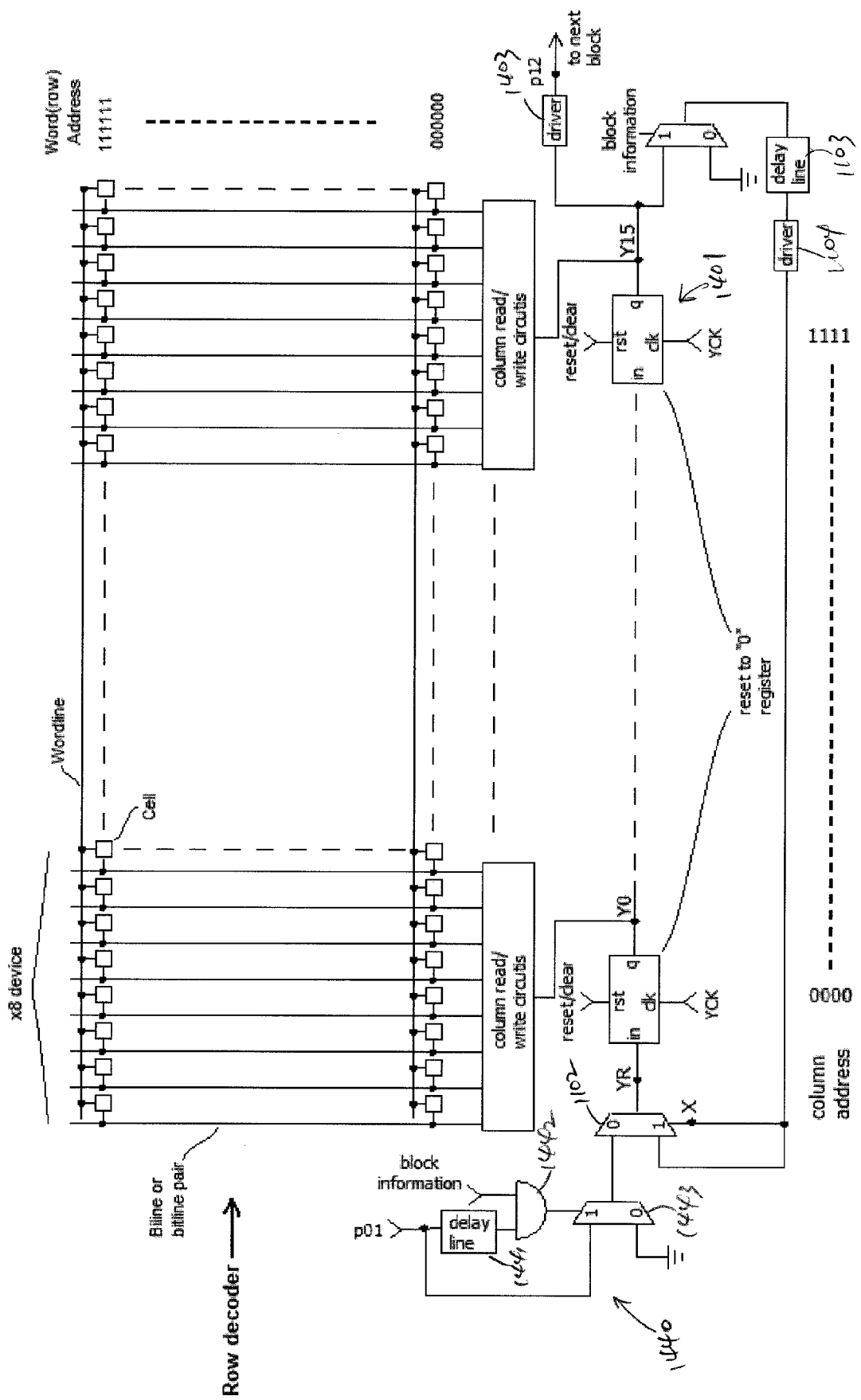

FIG. 13B shows memory array 1340 provided as n blocks. As shown in FIG. 13B, one addressing sequence addresses all memory cells of one block before addressing the next block (FIG. 13B). Such an addressing scheme may be supported by the shift register structure 1401 in each of FIGS. 14A and 14B. FIGS. 14A and 14B show, respectively, shift register structures for a memory block with a single section and any of the subsequent blocks. As shown in FIG. 14A, instead of rotating the '1' bit at output bit $Y_{15}$ after the $16^{th}$ cycle, as shown in FIG. 9, the '1' bit may be forwarded by driver 1403 to the input node of the register element corresponding to bit $Y_0$ in the next block. Mulitplexer 1402 blocks rotation of the '1' bit back to the output bit $Y_0$ of the same block according to control signal "block information". The forwarded bit is provided to circuit 1440 of FIG. 14B. Circuit 1440 includes multiplexer 1443 that provides the '1' bit into the next section, when selected by the corresponding "block information". The forwarded '1' bit is delayed by delay element 1441 to meet the hold time requirement at node YR, as discussed above.

FIG. 13C shows memory array 1350 organized into blocks and, within each block, into sections. An addressing sequence may be constructed in which, with each block, a word line is activated in each section as the memory is accessed section by section; however, every memory cell in a block is accessed prior to accessing the next block. Such an accessing scheme can be provided by combining the approaches discussed above with respect to FIGS. 13A and 13B.

Figure 15:
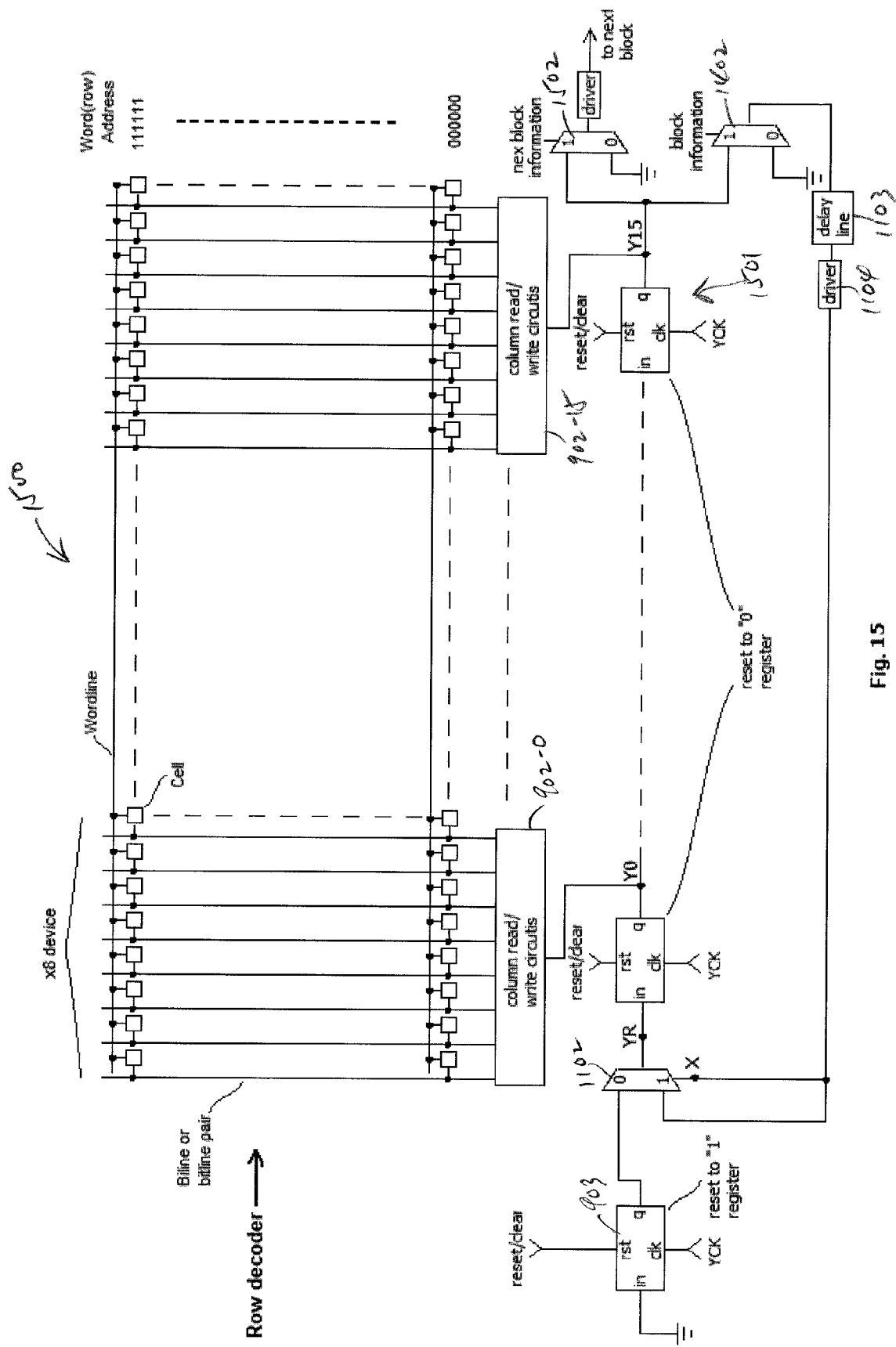
FIG. 15 shows an alternative shift register structure, according to one embodiment of the present invention.

FIG. 15 provides an alternative shift register structure to that shown in FIG. 14A, by including additional multiplexer 1502.

Figure 16:
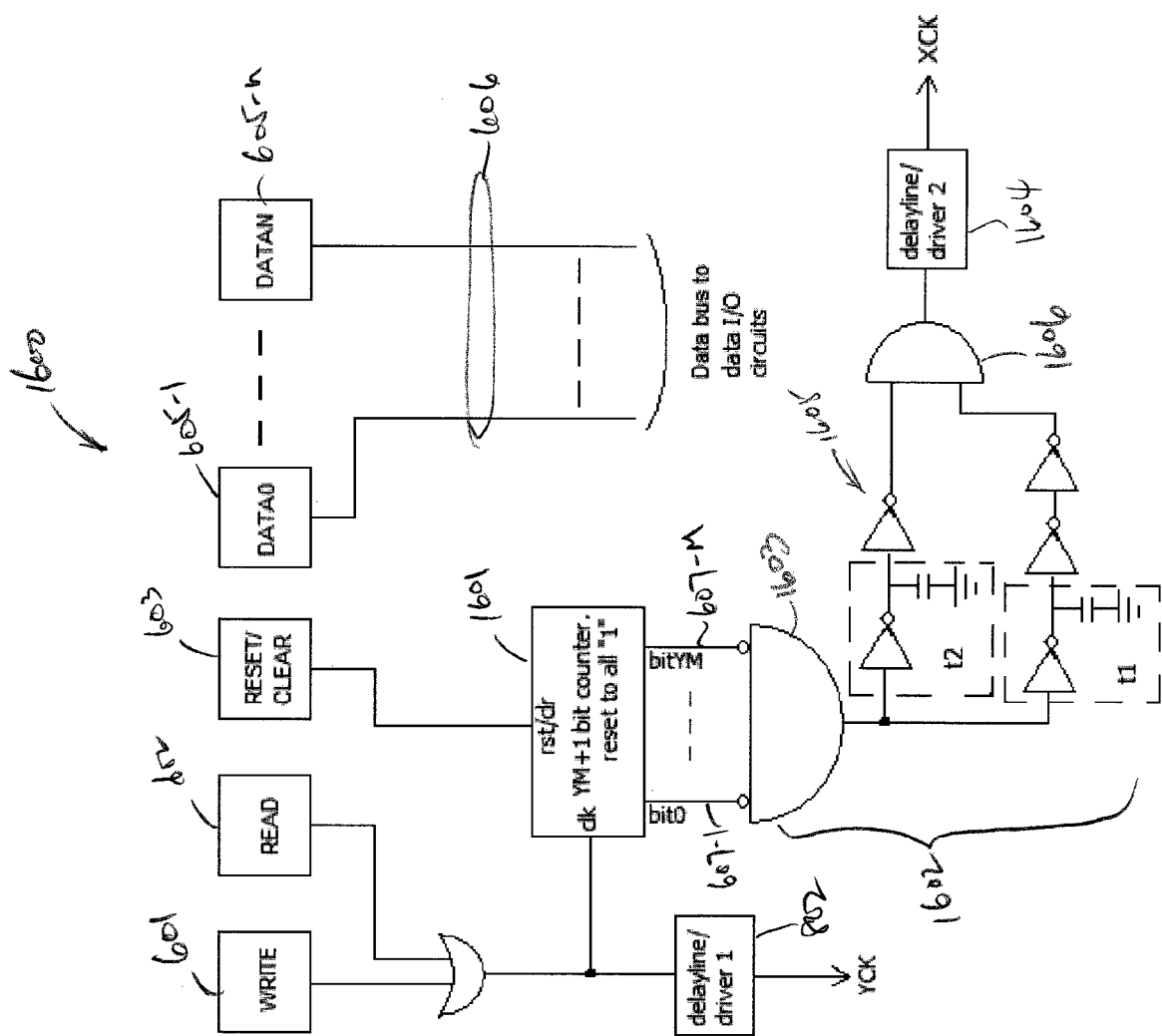
FIG. 16 shows address circuit 1600 in which decoded row address signals are provided by a shift register, in accordance with one embodiment of the present invention.

A shift register can also be used to replace the conventional row decoder. FIG. 16 shows address circuit 1600 in which decoded row address signals are provided by a shift register in the manners similar to those discussed above for the column addresses. As shown in FIG. 16, the row address bits output by counter 1601 are used to create clock pulses for a shift register to drive the word lines of a memory array. Initially, counter 1601 is reset by a pulse from reset or clear terminal 603 to all '1's. At the first write pulse on write terminal 601, the output signals of counter 1601 become all '0's, so that the output signal of NAND gate 1603 becomes '1'. Pulse generator 1605 includes two signal paths of delays $t_1$ and $t_2$, both greater than the clock to output delay of counter 1601, to avoid propagating glitches downstream. Delay $t_1$ is greater than delay $t_2$, such that the '0' value arriving over path of delay $t_1$ resets the '1' output of AND gate 1606 to provide clock pulse XCK. Clock pulse XCK is delayed by delay element 1604 to provide self-timing.

Figure 17:
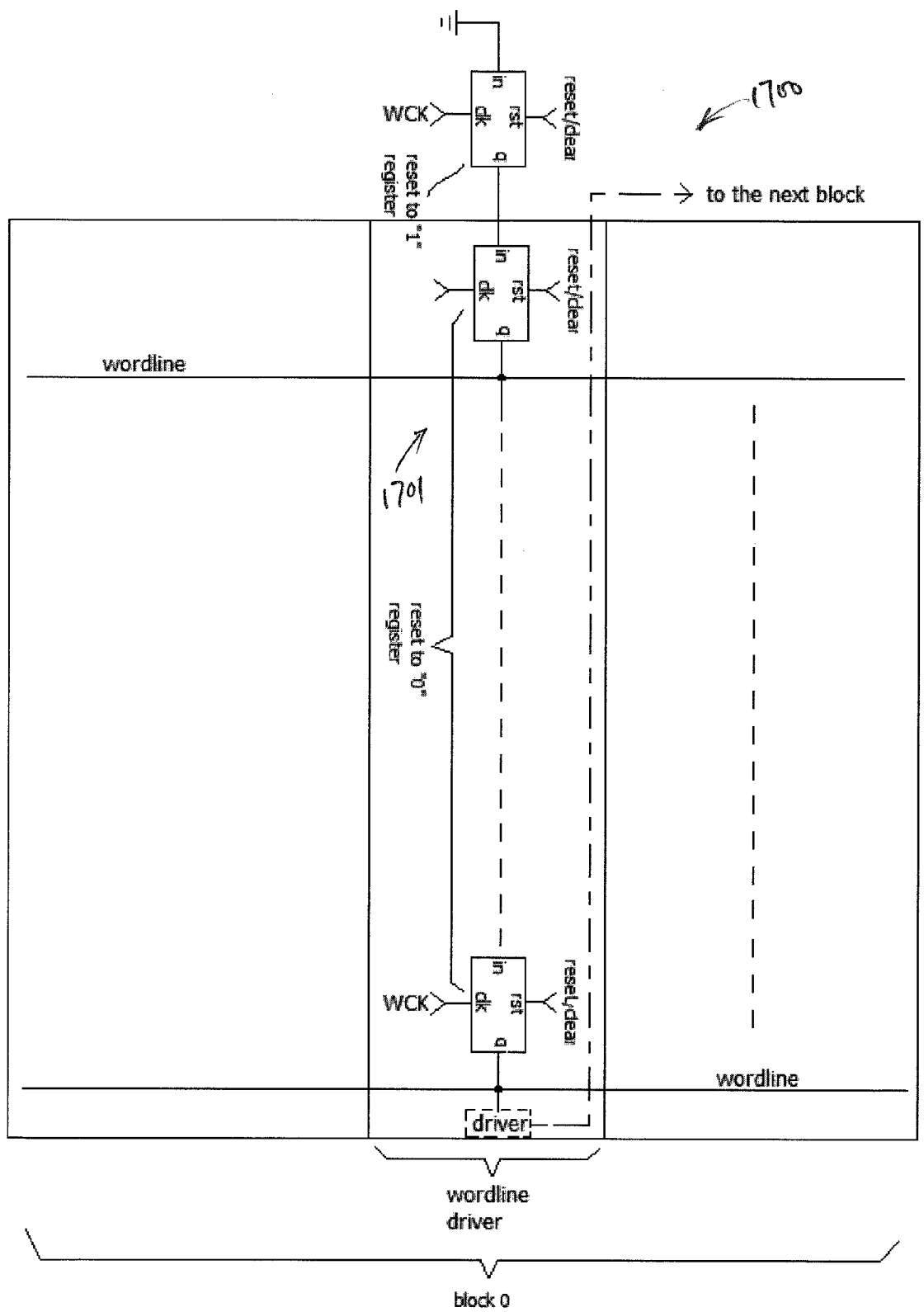
FIG. 17 shows shift register 1701 being driven by a clock pulse to activate successively word lines in memory block 1700.
Figure 18:
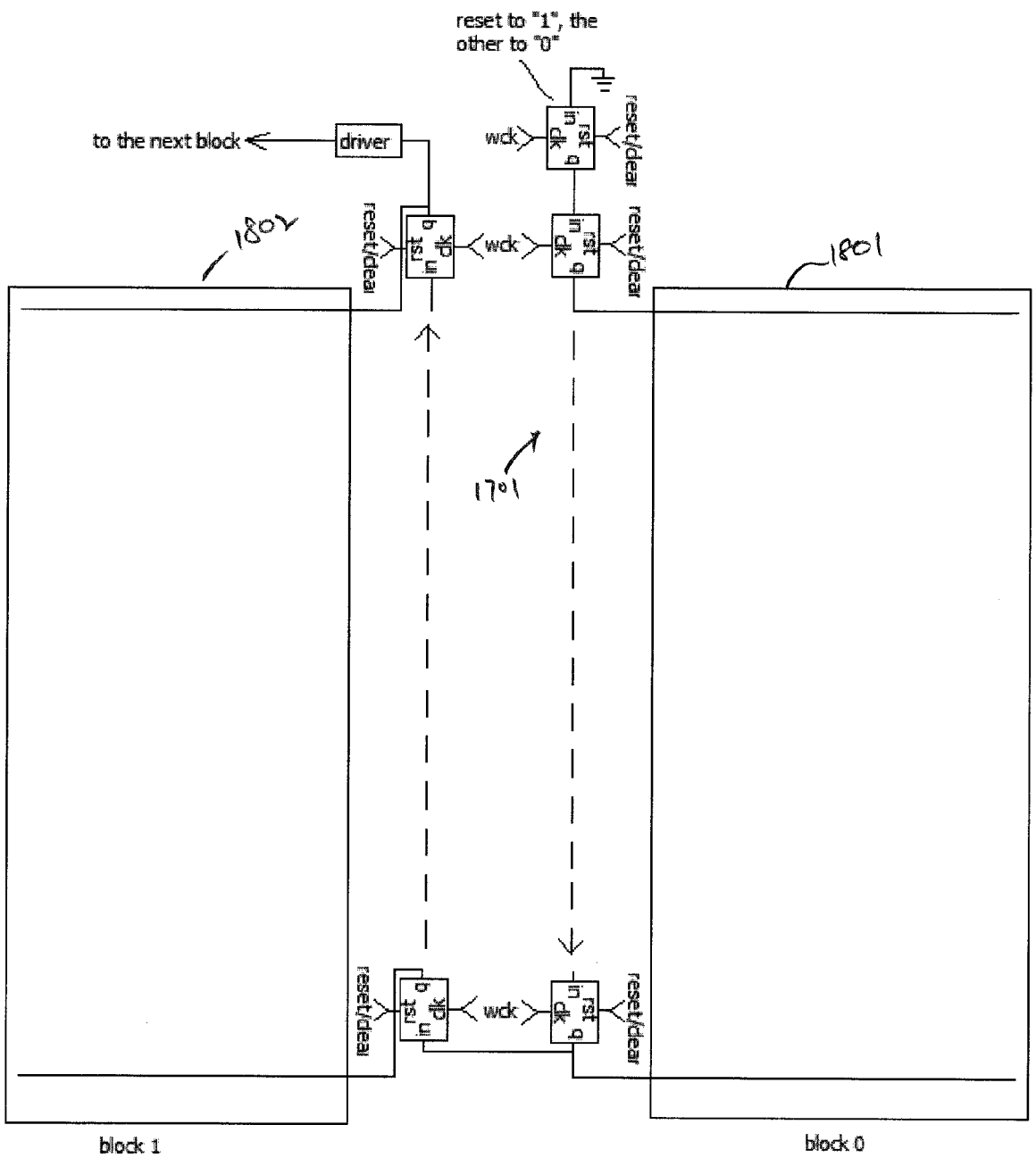
FIG. 18 shows a configuration of memory blocks 1801 and 1802 having their word lines controlled by shift registers 1803a and 1803b chained together to form shift register 1803.
Figure 19:
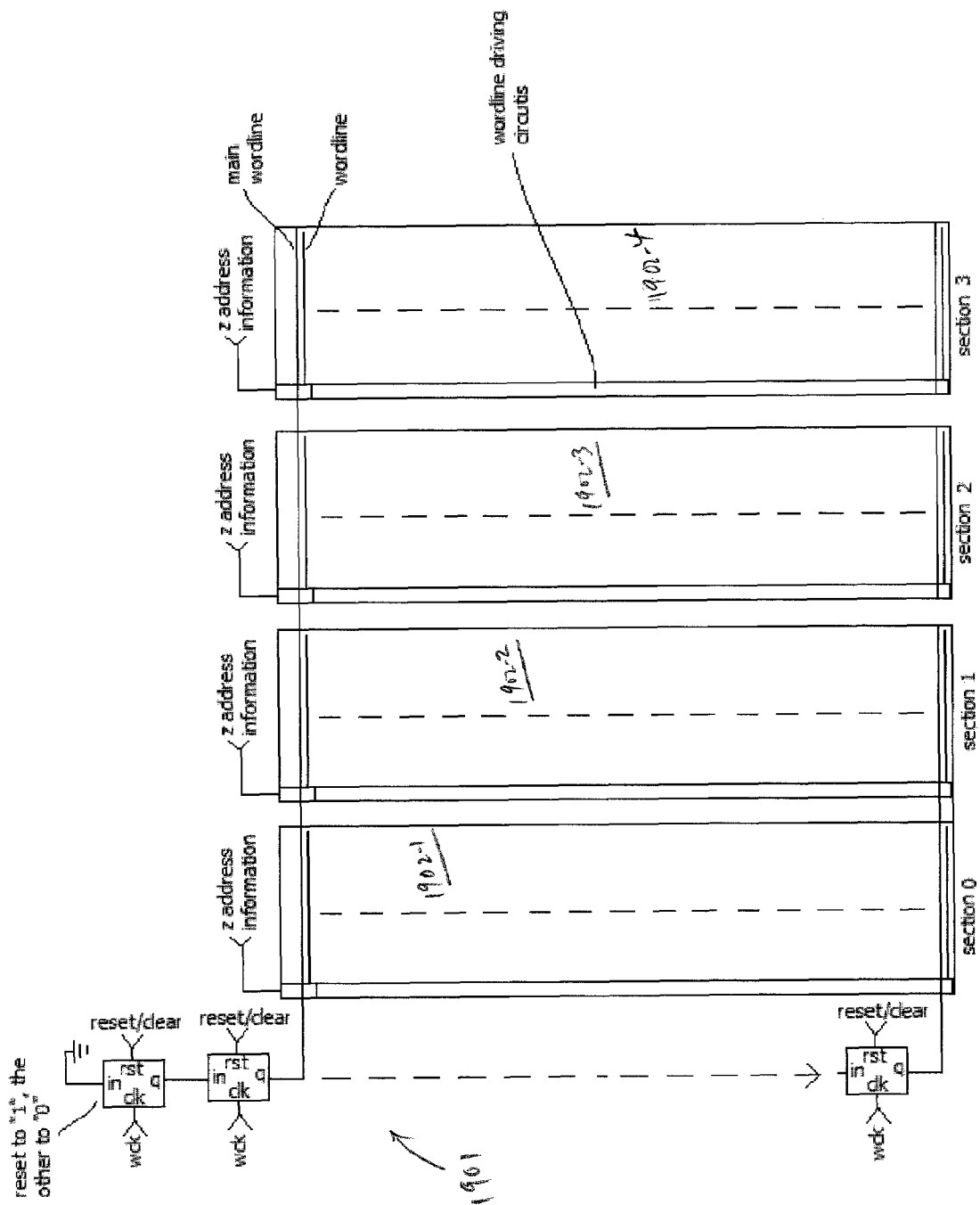
FIG. 19 shows configuration 1900 in which each bit of shift register 1901 controls a word line in each of sections 1902-1 to 1902-4, in accordance with one embodiment of the present invention.

FIG. 17 shows shift register 1701 being driven by such a clock pulse to activate successively word lines in memory block 1700. As shown in FIG. 17, the last output bit of shift register 1701 may be forwarded to the next block, so that the word line shift registers of many blocks may be chained together to form a long shift register that controls the word lines of multiple blocks. Such a multi-block configuration is shown in FIG. 18. In the configuration of FIG. 18, the word lines of memory block 1802 are activated after all the word lines of memory block 1801 have been activated. As discussed above, within a block, corresponding word lines of all blocks may be activated simultaneously. FIG. 19 shows one such configuration, in which each bit of shift register 1901 controls a word line ("main word line") that runs through sections 1902-1 to 1902-4 of a block. The loads on the main word line are the driver circuits for the actual word lines in each section; the actual word lines are coupled to the memory cells in each section. The "z-address bits" selectively activates the actual word line in each section (in this example, the z-address may be provided by two lower row address bits). In this manner, power is dissipated primarily only in the activated actual word line.

By replacing both row and column decoder circuits by shift registers, even greater power and silicon area advantages are achieved. In fact, the technique described above may be applied to any portion of block, row and column address decoding. In some embodiment, by providing different addressing sequences for read and write operations, a memory device for the capsule camera may be programmed for different applications that require different tradeoffs between resolution and length of recording time. For example, addressing sequences may be programmed during manufacturing by tying configuration bits to predetermined states. Thus, the same ASIC may be customized, for example, for different small intestine and large intestine programs which may require different collection times or image resolutions, thereby saving development costs and turn around time. With data compression and the memory device of the present invention, using semiconductor memories within the space constraint of the capsule has become feasible. Various data compression schemes are possible. As one example, compression of still images under the JPEG[3] standard may be modified to allowing a comparison between successive still images and encoding the difference from image to image. As another example, compression under the MPEG[4] standard may be used. Using a combination of JPEG and MPEG techniques is also possible.

[3] JPEG stands for "Joint Photography Expert Group."
[4] MPEG stands for "Motion Picture Expert Group."

Additional power saving techniques can be applied. For example, the capsule camera may operate in different power modes, such as "off" "on", "sleep", "monitor", or "wake-up", according to the level of activities. A schedule of operation based on elapsed time is also possible. For example, activities may be scheduled according to the estimated times the capsule will require to travel through the esophagus, the stomach, the small intestine, and the large intestine. Time elapsed estimates may be obtained empirical by studying a large number of patients. With reliable time estimates, the capsule camera may be activated by a timer circuit when it reaches the stomach. Alternatively, the position of the capsule may be detected using secondary sensors, such as pH, pressure and temperature. Depending on the region where the physician desires imaging, only the selected region is imaged, so that the limited amount of semiconductor memory may be dedicated for high definition imaging for that region. Different modes and different activation schemes are also possible.

The detailed description above is provided to illustrate the specific embodiments of the present invention and is not intended to be limiting. Numerous modifications and variations within the scope of the present invention are possible. The present invention is set forth in the following claims.

I claim:

1. A semiconductor memory device, comprising:
    a memory array comprising a plurality of memory cells, each memory cell being addressed by selectively activating one of a plurality word lines and one of a plurality of bit lines;
    an input for receiving a clock signal;
    a counter for providing successively a plurality of addresses according to a predetermined sequence in response to the clock signal;
    a first address circuit that receives the addresses and activates word lines corresponding to the addresses;
    a second address circuit that activates bit lines; and
    a register provided between the output terminals of the counter and the first address circuit, the register providing each of the addresses to the first address circuit after a predetermined delay from the clock signal.

2. A semiconductor device as in claim 1, wherein the second address circuit activates each of the plurality of bit lines in sequence in response to the clock signal.

3. A semiconductor device as in claim 2, wherein the second address circuit receives the clock signal after a predetermined delay.

4. A semiconductor device as in claim 2, wherein the second address circuit comprises a shift register.

5. A semiconductor device as in claim 3, wherein the memory array comprises a memory block including a plurality of sections, each section comprising driver circuits for activating word line within the section that are separate from driver circuits for word lines in another section.

6. A semiconductor device as in claim 5, wherein the second address circuit comprises a shift register activating bit lines for multiple sections.

7. A semiconductor device as in claim 5, wherein the counter generates an address sequence that accesses the sections in sequence, moving from one section to a next section after all memory cells corresponding to only a single word line of the one section is accessed.

8. A semiconductor device as in claim 5, wherein the memory block is one of a plurality of memory blocks and wherein the counter generates an address sequence that accesses the memory blocks in sequence, moving from one block to a next block after all memory cells in the one block are accessed.

9. A semiconductor device as in claim 1, wherein the counter comprises a Gray counter.

10. A semiconductor device as in claim 1, wherein memory cells comprise non-volatile memory cells.

11. A semiconductor device as in claim 1, wherein the memory cells comprise volatile memory cells.

12. A semiconductor device, comprising:
   a memory array comprising a plurality of memory cells, each memory cell being addressed by selectively activating one of a plurality word lines and one of a plurality of bit lines;
   an input for receiving a clock signal;
   a counter for providing successively a plurality of addresses according to a predetermined sequence in response to the clock signal;
   a first address circuit that receives the addresses and activates word lines corresponding to the addresses; and
   a second address circuit that activates bit lines, wherein the first address circuit comprises a shift register and a pulse generator which provides a pulse in response to a predetermined address generated by the counter.

13. A semiconductor device as in claim 12, wherein the pulse from the pulse generator has a first signal transition after a predetermined delay from the clock signal.

14. A semiconductor device as in claim 1, wherein the semiconductor memory device is embedded in a capsule camera apparatus comprising:
   a housing adapted to be swallowed;
   a light source within the housing; and
   a camera within the housing for capturing a first digital image and a second digital image of a scene illuminated by the light source.

15. A semiconductor device as in claim 14, wherein the capsule camera apparatus further comprising:
   a motion detector that detects a motion based on a difference between the first digital image and the second digital image; and
   a motion evaluator that determines whether or not the second digital image is stored in the semiconductor device.

16. A semiconductor device as in claim 14, wherein the capsule camera apparatus further comprises an output port for accessing the semiconductor device for uploading contents of the memory cell.

17. A semiconductor device as in claim 16, wherein the memory cells of the semiconductor device are accessed through the output port without specifying an address.

18. A semiconductor device as in claim 14, wherein a program for an operation of the capsule camera apparatus is provided in the semiconductor device prior to the capsule camera apparatus is swallowed by a patient.

19. A semiconductor device as in claim 14, further comprising one or more sensors for detecting one or more environmental parameters.

20. A method for accessing a semiconductor memory device, comprising:
   providing a memory array comprising a plurality of memory cells, each memory cell being addressed by selectively activating one of a plurality word lines and one of a plurality of bit lines;
   providing a clock signal to a counter to successively generate a plurality of addresses according to a predetermined sequence;
   providing a register between the output terminals of the counter and a first address circuit, the register providing each of the addresses after a predetermined delay from the clock signal;
   using the addresses generated by the counter to cause the first address circuit to activate word lines corresponding to the addresses; and
   activating bit lines using a second address circuit.

21. A method as in claim 20, wherein the second address circuit activates each of the plurality of bit lines in sequence in response to the clock signal.

22. A method as in claim 21, wherein the second address circuit receives the clock signal after a predetermined delay.

23. A method as in claim 21, wherein a shift register in the second address circuit activates the bit lines one at a time in sequence.

24. A method as in claim 22, wherein the memory array comprises a memory block including a plurality of sections, each section comprising driver circuits for activating word line within the section that are separate from driver circuits for word lines in another section.

25. A method as in claim 24, further comprising, using a shift register in the second address circuit, activating the bit lines of multiple sections one at a time in sequence.

26. A method as in claim 24, further comprising generating in the counter an address sequence that accesses the sections in sequence, moving from one section to a next section after all memory cells corresponding to only a single word line of the one section is accessed.

27. A method as in claim 24, wherein the memory block is one of a plurality of memory blocks in the memory array, the method further comprising generating in the counter an address sequence that accesses the memory blocks in sequence, moving from one memory block to a next memory block after all memory cells in the one memory block are accessed.

28. A method as in claim 20, wherein the counter comprises a Gray counter.

29. A method as in claim 20, wherein the memory cells comprise non-volatile memory cells.

30. A method as in claim 20, wherein the memory cells comprise volatile memory cells.

31. A method for accessing a semiconductor memory device, comprising:
   providing a memory array comprising a plurality of memory cells, each memory cell being addressed by selectively activating one of a plurality word lines and one of a plurality of bit lines;
   providing a clock signal to a counter to successively generate a plurality of addresses according to a predetermined sequence;
   using the addresses generated by the counter to cause the first address circuit to activate word lines corresponding to the addresses; and
   activating bit lines using a second address circuit, wherein the first address circuit shifts a set bit through a shift register and generates a pulse in response to a predetermined address generated by the counter.

32. A method as in claim 31, wherein the pulse has a first signal transition after a predetermined delay from the clock signal.

33. A method as in claim 20, wherein the semiconductor memory device is embedded in a capsule camera apparatus comprising:
   a housing adapted to be swallowed;
   a light source within the housing; and
   a camera within the housing for capturing a first digital image and a second digital image of a scene illuminated by the light source.

34. A method as in claim 33, further comprising:
   detecting a motion based on a difference between the first digital image and the second digital image; and
   determining whether or not the second digital image is stored in the semiconductor device.

35. A method as in claim 33, further comprising accessing the semiconductor device through an output port of the capsule camera to upload contents of the memory cell.

36. A method as in claim 35, wherein the memory cells of the semiconductor device are accessed through the output port without specifying an address.

37. A method as in claim 33, further comprising providing a program for an operation of the capsule camera apparatus in the semiconductor device prior to the capsule camera apparatus is swallowed by a patient.

38. A method as in claim 33, further comprising receiving signals from one or more sensors for detecting one or more environmental parameters relevant to determining an operating mode of the capsule camera apparatus.

* * * * *